United States Patent
Marasco et al.

(10) Patent No.: US 10,463,732 B2
(45) Date of Patent: Nov. 5, 2019

(54) GLUCOCORTICOID-INDUCED TUMOR NECROSIS FACTOR RECEPTOR (GITR) ANTIBODIES AND METHODS OF USE THEREOF

(71) Applicant: Dana-Farber Cancer Institute, Inc., Boston, MA (US)

(72) Inventors: Wayne A. Marasco, Wellesley, MA (US); Chen Xu, Beijing (CN); De-Kuan Chang, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 15/516,272

(22) PCT Filed: Oct. 5, 2015

(86) PCT No.: PCT/US2015/054010
§ 371 (c)(1),
(2) Date: Mar. 31, 2017

(87) PCT Pub. No.: WO2016/054638
PCT Pub. Date: Apr. 7, 2016

(65) Prior Publication Data
US 2017/0304444 A1     Oct. 26, 2017

Related U.S. Application Data

(60) Provisional application No. 62/059,458, filed on Oct. 3, 2014.

(51) Int. Cl.
*A61K 39/395*    (2006.01)
*C07K 16/28*    (2006.01)
*A61K 39/00*    (2006.01)

(52) U.S. Cl.
CPC .... *A61K 39/39558* (2013.01); *C07K 16/2878* (2013.01); *A61K 39/00* (2013.01); *C07K 2317/92* (2013.01)

(58) Field of Classification Search
CPC .............. A61K 39/39558; A61K 39/00; C07K 16/2878; C07K 2317/92
See application file for complete search history.

(56) References Cited

U.S. PATENT DOCUMENTS

| | | | |
|---|---|---|---|
| 3,773,919 A | 11/1973 | Boswell et al. | |
| 4,485,045 A | 11/1984 | Regen | |
| 4,522,811 A | 6/1985 | Eppstein et al. | |
| 4,544,545 A | 10/1985 | Ryan et al. | |
| 4,676,980 A | 6/1987 | Segal et al. | |
| 4,816,567 A | 3/1989 | Cabilly et al. | |
| 4,946,778 A | 8/1990 | Ladner et al. | |
| 5,013,556 A | 5/1991 | Woodle et al. | |
| 5,030,719 A | 7/1991 | Umemoto et al. | |
| 5,091,513 A | 2/1992 | Huston et al. | |
| 5,132,405 A | 7/1992 | Huston et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 5,916,771 A | 6/1999 | Hori et al. | |
| 5,939,598 A | 8/1999 | Kucherlapati et al. | |

FOREIGN PATENT DOCUMENTS

| | | |
|---|---|---|
| WO | 1991/00360 | 1/1991 |
| WO | 1994/02602 | 2/1994 |
| WO | 1994/011026 | 5/1994 |
| WO | 1995/22618 | 8/1995 |
| WO | 1996/33735 | 10/1996 |
| WO | 1996/34096 | 10/1996 |
| WO | 1999/53049 | 10/1999 |
| WO | 2005/018572 | 3/2005 |
| WO | 2005/047327 | 5/2005 |
| WO | 2006/105021 A2 | 10/2006 |
| WO | 2007/133822 A1 | 11/2007 |
| WO | 2011/028683 A1 | 3/2011 |
| WO | 2013/039954 A1 | 3/2013 |

OTHER PUBLICATIONS

Antibodies—A, Harlow E. Lane D. "Laboratory Manual." (1988).
Barbas, Carlos F., et al. "Recombinant human Fab fragments neutralize human type 1 immunodeficiency virus in vitro." Proceedings of the National Academy of Sciences 89.19 (1992): 9339-9343.
Bobo, R. Hunt, et al. "Convection-enhanced delivery of macromolecules in the brain." Proceedings of the National Academy of Sciences 91.6 (1994): 2076-2080.
Brodeur, Bernard R., et al. "Mouse-human myeloma partners for the production of heterohybridomas." Chapter 4 (1987): 51-63.
Caron, Philip C., et al. "Engineered humanized dimeric forms of IgG are more effective antibodies." Journal of Experimental Medicine 176.4 (1992): 1191-1195.
Cole, S. P. C. "Monoclonal Antibodies and Cancer Therapy, Alan R. Liss." Inc., New York, New York (1985): 77-96.
Cote, Richard J., et al. "Generation of human monoclonal antibodies reactive with cellular antigens." Proceedings of the National Academy of Sciences 80.7 (1983):2026-2030.
Cruse, J. M., and R. E. Lewis Jr. "Conjugate vaccines. Contributions to microbiology and immunology." (1989).
Davidson, Beverly L., et al. "A model system for in vivo gene transfer into the central nervous system using an adenoviral vector." Nature genetics 3.3 (1993): 219.
Davies, David R., Eduardo A. Padlan, and Steven Sheriff. "Antibody-antigen complexes." Annual review of biochemistry 59.1 (1990): 439-473.
Diamandis, Eleftherios P., and Theodore K. Christopoulos, eds. Immunoassay. Academic Press, 1996.

(Continued)

*Primary Examiner* — Ruixiang Li

(57) ABSTRACT

The present invention comprises human monoclonal antibodies that bind to GITR (also known as glucocorticoid-induced tumor necrosis factor receptor). Binding of the invented antibody to GITR inhibits binding of its ligand, GITR-L, and can be used to treat cancer.

12 Claims, 5 Drawing Sheets

Specification includes a Sequence Listing.

(56) References Cited

OTHER PUBLICATIONS

Eppstein, Deborah A., et al. "Biological activity of liposome-encapsulated murine interferon gamma is mediated by a cell membrane receptor." Proceedings of the National Academy of Sciences 82.11 (1985): 3688-3692.
Fishwild, Dianne M., et al. "High-avidity human IgG? monoclonal antibodies from a novel strain of minilocus transgenic mice." Nature biotechnology 14.7 (1996): 845.
Geller, Alfred I., and Andrew Freese. "Infection of cultured central nervous system neurons with a defective herpes simplex virus 1 vector results in stable expression of Escherichia coli beta-galactosidase." Proceedings of the National Academy of Sciences 87.3 (1990): 1149-1153.
Geller, Alfred I., et al. "An HSV-1 Vector Expressing Tyrosine Hydroxylase Causes Production and Release of I-DOPA from Cultured Rat Striatal Cells." Journal of neurochemistry 64.2 (1995): 487-496.
Geller, Alfred I., et al. "Long-term increases in neurotransmitter release from neuronal cells expressing a constitutively active adenylate cyclase from a herpes simplex virus type 1 vector." Proceedings of the National Academy of Sciences 90.16 (1993): 7603-7607.
Goding, Monoclonal Antibodies. "Principles and Practice 2nd ed., Chapter 3: Production of Monoclonal Antibodies, 1986." 59-103.
Hoogenboom, Hennie R., and Greg Winter. "By-passing immunisation: human antibodies from synthetic repertoires of germline VH gene segments rearranged in vitro." Journal of molecular biology 227.2 (1992): 381-388.
Huse, William D., et al. "Generation of a large combinatorial library of the immunoglobulin repertoire in phage lambda." Science 246. 4935 (1989): 1275-1281.
Huston, James S., et al. "Protein engineering of antibody binding sites: recovery of specific activity in an anti-digoxin single-chain Fv analogue produced in Escherichia coli." Proceedings of the National Academy of Sciences 85.16 (1988): 5879-5883.
Hwang, Karl J., K. F. Luk, and Paul L. Beaumier. "Hepatic uptake and degradation of unilamellar sphingomyelin/cholesterol liposomes: a kinetic study." Proceedings of the National Academy of Sciences 771 (1980): 4030-4034.
Kaplitt, Michael G., et al. "Long-term gene expression and phenotypic correction using adeno-associated virus vectors in the mammalian brain." Nature genetics 8.2 (1994): 148.
Killen, J. A., and J. M. Lindstrom. "Specific killing of lymphocytes that cause experimental autoimmune myasthenia gravis by ricin toxin-acetylcholine receptor conjugates." The Journal of Immunology 133.5 (1984): 2549-2553.
Kohler, Georges, and Cesar Milstein. "Continuous cultures of fused cells secreting antibody of predefined specificity." nature256.5517 (1975): 495.
Kozbor, Danuta, and John C. Roder. "The production of monoclonal antibodies from human lymphocytes." Immunology Today 4.3 (1983): 72-79.
Kozbor, Danuta, et al. "A human hybrid myeloma for production of human monoclonal antibodies." The Journal of Immunology 133.6 (1984): 3001-3005.
La Salle, G. Le Gal, et al. "An adenovirus vector for gene transfer into neurons and glia in the brain." Science 259.5097 (1993): 988-990.
Labrijn, Aran F., et al. "Species-specific determinants in the IgG CH3 domain enable Fab-arm exchange by affecting the noncovalent CH3—CH3 interaction strength." The Journal of Immunology 187.6 (2011): 3238-3246.
Lam, Kit S. "Mini-review. Application of combinatorial library methods in cancer research and drug discovery." Anti-cancer drug design 12.3 (1997): 145-167.
Lim, F., et al., in DNA Cloning: Mammalian Systems, D. Glover, Ed. (Oxford Univ. Press, Oxford England) (1995).
Lonberg, Nils, and Dennis Huszar. "Human antibodies from transgenic mice." International reviews of immunology 13.1 (1995): 65-93.
Lonberg, Nils, et al. "Antigen-specific human antibodies from mice comprising four distinct genetic modifications." Nature 368.6474 (1994): 856.
Malmqvist, Magnus. "Biospecific interaction analysis using biosensor technology." Nature 361.6408 (1993): 186-187.
Marasco, Wayne A., William A. Haseltine, and SiYi Chen. "Design, intracellular expression, and activity of a human anti-human immunodeficiency virus type 1 gp120 single-chain antibody." Proceedings of the National Academy of Sciences 90.16 (1993): 7889-7893.
Marks, James D., et al. "By-passing immunization: human antibodies from V-gene libraries displayed on phage." Journal of molecular biology 222.3 (1991): 581-597.
Marks, James D., et al. "By-Passing Immunization: Building High Affinity Human Antibodies by Chain Shuffling." Bio/technology 10.7 (1992): 779.
Martin, Francis J., and Demetrios Papahadjopoulos. "Irreversible coupling of immunoglobulin fragments to preformed vesicles. An improved method for liposome targeting." Journal of Biological Chemistry 257.1 (1982): 286-288.
Morrison, Sherie L. "Immunology-Success in Specification." Nature 368.6474 (1994): 812-813.
Muldoon, Mark T. ELISA: Theory and practice. Methods in molecular biology, vol. 42: by John R. Crowther. Totowa, Humana, 1995.
Munson, Peter J., and David Rodbard. "Ligand: a versatile computerized approach for characterization of ligand-binding systems." Analytical biochemistry 107.1 (1980): 220-239.
Neuberger, Michael. "Generating high-avidity human Mabs in mice." Nature biotechnology 14.7 (1996): 826.
Ramakrishnan, S., and L. L. Houston. "Comparison of the selective cytotoxic effects of immunotoxins containing ricin A chain or pokeweed antiviral protein and anti-Thy 1.1 monoclonal antibodies." Cancer research 44.1 (1984): 201-208.
Ridgway, John BB, Leonard G. Presta, and Paul Carter. "'Knobs-into-holes' engineering of antibody CH3 domains for heavy chain heterodimerization." Protein Engineering, Design and Selection 9.7 (1996): 617-621.
Shopes, Bob. "A genetically engineered human IgG mutant with enhanced cytolytic activity." The Journal of Immunology 148.9 (1992): 2918-2922.
Stevenson, G. T., A. Pindar, and C. J. Slade. "A chimeric antibody with dual Fc regions (bisFabFc) prepared by manipulations at the IgG hinge." Anti-cancer drug design 3.4 (1989): 219-230.
Van der Neut Kolfschoten, Marijn, et al. "Anti-inflammatory activity of human IgG4 antibodies by dynamic Fab arm exchange." Science 317.5844 (2007): 1554-1557.
Vitetta, Ellen S., et al. "Redesigning nature's poisons to create anti-tumor reagents." Science 238.4830 (1987): 1098-1104.
Wilkinson, D. "Ultimate abs-Immunochemical techniques inspire development of new antibody purification methods." Scientist 14.8 (2000): 25-28.
Yang, Yiping, et al. "Cellular and humoral immune responses to viral antigens create barriers to lung-directed gene therapy with recombinant adenoviruses." Journal of virology 69.4 (1995): 2004-2015.
Zebedee, Suzanne L., et al. "Human combinatorial antibody libraries to hepatitis B surface antigen." Proceedings of the National Academy of Sciences 89.8 (1992): 3175-3179.

Figure 3

| # | 1 | 3 | 5 | 7 | 10 | 11 | 12 | 13 | 14 | 15 | 17 |
|---|---|---|---|---|----|----|----|----|----|----|----|
| $K_{on}$ | 2.85E+06 | 2.51E+06 | 2.84E+06 | 2.84E+05 | 1.06E+06 | 2.76E+06 | 9.22E+06 | 3.32E+06 | 2.75E+06 | 1.76E+06 | 6.58E+06 |
| $K_{off}$ | 7.14E-03 | 2.34E-03 | 7.72E-05 | 5.89E-04 | 6.56E-03 | 1.02E-02 | 9.24E-02 | 1.24E-02 | 6.14E-03 | 7.71E-03 | 8.74E-03 |
| $K_D$ | 1.66E-09 | 8.55E-10 | 4.20E-10 | 3.13E-09 | 4.77E-09 | 2.80E-09 | 5.065E-09 | 3.21E-09 | 1.82E-09 | 3.81E-09 | 1.14E-09 |

SEQUENCE LISTING

<160> NUMBER OF SEQ ID NOS: 110

<210> SEQ ID NO 1
<211> LENGTH: 360
<212> TYPE: DNA
<213> ORGANISM: Artificial Sequence
<220> FEATURE:
<223> OTHER INFORMATION: Synthetic Polynucleotide

<400> SEQUENCE: 1

```
gaggtgcagc tggtggagtc tggggctgag gtgaagaagc ctggggcctc agtgaaggtc      60
tcctgcaaga cttctggata caccttcacc gaccactata tccactgggt gcgacaggcc     120
cctggacaag gcttgagtg gatgggatgg atcaaccctg gcagtggtgg cacagagtat      180
gcacagaagt tcagggcag gtcaccatg accaggaca cgcccattag cacggcctac        240
atggatctga gcgggctgag atctgacgac acggccgttt attactgtgc gagagagact     300
atcggtggct ggaacgcttt ggacgtctgg ggccaaggaa ccctggtcac cgtctcctca     360
```

<210> SEQ ID NO 2
<211> LENGTH: 120
<212> TYPE: PRT
<213> ORGANISM: Artificial Sequence
<220> FEATURE:
<223> OTHER INFORMATION: Artificial Polypeptide

<400> SEQUENCE: 2

Glu Val Gln Leu Val Glu Ser Gly Ala Glu Val Lys Lys Pro Gly Ala
1               5                   10                  15

Ser Val Lys Val Ser Cys Lys Thr Ser Gly Tyr Thr Phe Thr Asp His
            20                  25                  30

Tyr Ile His Trp Val Arg Gln Ala Pro Gly Gln Gly Leu Glu Trp Met
        35                  40                  45

Gly Trp Ile Asn Pro Ser Gly Gly Thr Glu Tyr Ala Gln Lys Phe
    50                  55                  60

Gln Gly Arg Val Thr Met Thr Arg Asp Thr Pro Ile Ser Thr Ala Tyr
65                  70                  75                  80

Met Asp Leu Ser Gly Leu Arg Ser Asp Asp Thr Ala Val Tyr Tyr Cys
                85                  90                  95

Ala Arg Glu Thr Ile Gly Gly Trp Asn Ala Leu Asp Val Trp Gly Gln
            100                 105                 110

Gly Thr Leu Val Thr Val Ser Ser
        115                 120

<210> SEQ ID NO 3
<211> LENGTH: 333
<212> TYPE: DNA
<213> ORGANISM: Artificial Sequence
<220> FEATURE:
<223> OTHER INFORMATION: Artificial Polynucleotide

<400> SEQUENCE: 3

```
cagcctgtgc tgactcagcc accctcagcg tctgggaccc ccgggcagag ggtcaccatc      60
tcttgttctg gaagcagctc caacatcgga attaatactg taaactggta ccagcagctc     120
ccaagaacgc cccccaaact cctcatctat actaataatc agcggccctc aggggtccct     180
gaccgattct ctggctccaa gtctgacacc tcagcctccc tggccatcag tggcctccag     240
tctgaggatg aggctgatta ttactgtgca gcttgggatg acaccctgaa tggtccacta     300
ttcggcggag ggaccaaggt gaccgtccta ggt                                  333
```

```
<210> SEQ ID NO 4
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 4

Gln Pro Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ile Asn
            20                  25                  30

Thr Val Asn Trp Tyr Gln Gln Leu Pro Arg Thr Pro Pro Lys Leu Leu
        35                  40                  45

Ile Tyr Thr Asn Asn Gln Arg Pro Ser Gly Val Pro Asp Arg Phe Ser
    50                  55                  60

Gly Ser Lys Ser Asp Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Thr Leu
                85                  90                  95

Asn Gly Pro Leu Phe Gly Gly Gly Thr Lys Val Thr Val Leu Gly
            100                 105                 110

<210> SEQ ID NO 5
<211> LENGTH: 357
<212> TYPE: DNA
<213> ORGANISM: Artificial Sequence
<220> FEATURE:
<223> OTHER INFORMATION: Synthetic Polynucleotide

<400> SEQUENCE: 5
gaggtgcagc tggtgcagtc tgggtctgag ttgaagaagc ctggggcctc agtgaaggtc        60
tcctgcaagg cttctggata caccttcacc ggctactata tgcactgggt gcgacaggcc       120
cctggacaag gcttgagtg gatgggatgg atcaacccta acagtggtgg cacaaactat        180
gcacagaagt tcagggcag ggtcaccgtg accacagaca cgtccacgag cacagcctac        240
atggagctga ggagcctgag atctgacgac acggccgtct attactgtgc gagagggt        300 gttcactcgg atgcttttga tgtgtggggc caagggacca cggtcaccgt ctcctca          357

<210> SEQ ID NO 6
<211> LENGTH: 119
<212> TYPE: PRT
<213> ORGANISM: Artificial Sequence
<220> FEATURE:
<223> OTHER INFORMATION: Synthetic Polypeptide

<400> SEQUENCE: 6

Glu Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Val Thr Thr Asp Thr Ser Thr Ser Thr Ala Tyr
65                  70                  75                  80
```

```
Met Glu Leu Arg Ser Leu Arg Ser Asp Asp Thr Ala Val Tyr Tyr Cys
                85                  90                  95

Ala Arg Glu Gly Val His Ser Asp Ala Phe Asp Val Trp Gly Gln Gly
            100                 105                 110

Thr Thr Val Thr Val Ser Ser
        115

<210> SEQ ID NO 7
<211> LENGTH: 321
<212> TYPE: DNA
<213> ORGANISM: Artificial Sequence
<220> FEATURE:
<223> OTHER INFORMATION: Synthetic Polynucleotide

<400> SEQUENCE: 7
gaaacgacac tcacgcagtc tccagccacc ctgtctgtgt ctccagggga aagggccacc    60
ctctcctgca gggccagtca gagtgtttac accaacttag cctggtacca acagaaacct   120
ggccaggctc ccagtctcct catctatggt gcatccagcc gggccaccgg catcccagac   180
agattcagtg gcagcgggtc tgggacagac ttcactctca ccatcagcag actggagcct   240
gaagattttg cagtgtatta ctgtcagcag tatggtagct cacatttcac tttcggccct   300
gggaccaaag tggatatcaa a                                              321

<210> SEQ ID NO 8
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 8

Glu Thr Thr Leu Thr Gln Ser Pro Ala Thr Leu Ser Val Ser Pro Gly
1               5                   10                  15

Glu Arg Ala Thr Leu Ser Cys Arg Ala Ser Gln Ser Val Tyr Thr Asn
            20                  25                  30

Leu Ala Trp Tyr Gln Gln Lys Pro Gly Gln Ala Pro Ser Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser His Phe
                85                  90                  95

Thr Phe Gly Pro Gly Thr Lys Val Asp Ile Lys
            100                 105

<210> SEQ ID NO 9
<211> LENGTH: 360
<212> TYPE: DNA
<213> ORGANISM: Artificial Sequence
<220> FEATURE:
<223> OTHER INFORMATION: Synthetic Polynucleotide

<400> SEQUENCE: 9
gaggtgcagc tggtgcagtc tggggctgag gtgaagaagc ctggggcctc agtgaaggtc    60
tcctgcaaga cttctggata caccttcacc gaccactata tccactgggt gcgacaggcc   120
cctggacaag gcttgagtg gatgggatgg atcaaccct agcagtggtgg cacagagtat   180 gcacagaagt tcagggcag ggtcaccatg accagggaca cgcccattag cacggcctac   240
```

```
atggatctga gcgggctgag atctgacgac acggccgttt attactgtgc gagagagact    300
atcggtggct ggaacgcttt ggacgtctgg ggccaaggga ccacggtcac cgtctcctca    360
```

<210> SEQ ID NO 10
<211> LENGTH: 120
<212> TYPE: PRT
<213> ORGANISM: Artificial Sequence
<220> FEATURE:
<223> OTHER INFORMATION: Synthetic Polypeptide

<400> SEQUENCE: 10

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Asp His
            20                  25                  30

Tyr Ile His Trp Val Arg Gln Ala Pro Gly Gln Gly Leu Glu Trp Met
        35                  40                  45

Gly Trp Ile Asn Pro Ser Gly Gly Thr Glu Tyr Ala Gln Lys Phe
    50                  55                  60

Gln Gly Arg Val Thr Met Thr Arg Asp Thr Pro Ile Ser Thr Ala Tyr
65                  70                  75                  80

Met Asp Leu Ser Gly Leu Arg Ser Asp Asp Thr Ala Val Tyr Tyr Cys
                85                  90                  95

Ala Arg Glu Thr Ile Gly Gly Trp Asn Ala Leu Asp Val Trp Gly Gln
            100                 105                 110

Gly Thr Thr Val Thr Val Ser Ser
        115                 120

<210> SEQ ID NO 11
<211> LENGTH: 333
<212> TYPE: DNA
<213> ORGANISM: Artificial Sequence
<220> FEATURE:
<223> OTHER INFORMATION: Synthetic Polynucleotide

<400> SEQUENCE: 11

```
cagtctgtgc tgactcagcc accctcagcg tctgggtccc ccgggcagag ggtcaccatg     60
tcttgctctg gaagcagctc caccatcggg aggcattctg taaactggta ccagcagctc    120
ccaggaacgg ccccccaaact cctcatctat gctaacaatc agcggccctc aggggtccct    180
ggccgattct ctgcctccaa gtctgacacc tcagcctccc tggccatcag tgggctccgg    240
tccgaggatg aggctaatta ttactgtgca gcgtgggatg acagtctcag tggcgtgctc    300
tttggcggtg ggaccaaggt gaccgtccta ggt                                  333
```

<210> SEQ ID NO 12
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 12

Gln Ser Val Leu Thr Gln Pro Pro Ser Ala Ser Gly Ser Pro Gly Gln
1               5                   10                  15

Arg Val Thr Met Ser Cys Ser Gly Ser Ser Ser Thr Ile Gly Arg His
            20                  25                  30

Ser Val Asn Trp Tyr Gln Gln Leu Pro Gly Thr Ala Pro Lys Leu Leu
        35                  40                  45

```
Ile Tyr Ala Asn Asn Gln Arg Pro Ser Gly Val Pro Gly Arg Phe Ser
 50                  55                  60
Ala Ser Lys Ser Asp Thr Ser Ala Ser Leu Ala Ile Ser Gly Leu Arg
 65                  70                  75                  80
Ser Glu Asp Glu Ala Asn Tyr Tyr Cys Ala Ala Trp Asp Asp Ser Leu
                 85                  90                  95
Ser Gly Val Leu Phe Gly Gly Gly Thr Lys Val Thr Val Leu Gly
            100                 105                 110
```

<210> SEQ ID NO 13
<211> LENGTH: 360
<212> TYPE: DNA
<213> ORGANISM: Artificial Sequence
<220> FEATURE:
<223> OTHER INFORMATION: Synthetic Polynucleotide

<400> SEQUENCE: 13

```
gaggtgcagc tggtggagtc tggggctgag gtgaagaagc ctggggcctc agtgaaggtc    60
tcctgcaaga cttctggata caccttcacc gaccactata tccactgggt gcgacaggcc   120
cctggacaag gcttgagtg gatgggatgg atcaaccta gcagtggtgg cacagagtat   180
gcacagaagt ttcagggcag ggtcaccatg accagggaca cgcccattag cacggcctac   240
atggatctga gcgggctgag atctgacgac acggccgttt attactgtgc gagagagact   300
atcggtggct ggaacgcttt ggacgtctgg ggccaaggca ccctggtcac cgtctcctca   360
```

<210> SEQ ID NO 14
<211> LENGTH: 120
<212> TYPE: PRT
<213> ORGANISM: Artificial Sequence
<220> FEATURE:
<223> OTHER INFORMATION: Synthetic Polypeptide

<400> SEQUENCE: 14

```
Glu Val Gln Leu Val Glu Ser Gly Ala Glu Val Lys Lys Pro Gly Ala
  1               5                  10                  15
Ser Val Lys Val Ser Cys Lys Thr Ser Gly Tyr Thr Phe Thr Asp His
                 20                  25                  30
Tyr Ile His Trp Val Arg Gln Ala Pro Gly Gln Gly Leu Glu Trp Met
             35                  40                  45
Gly Trp Ile Asn Pro Ser Ser Gly Gly Thr Glu Tyr Ala Gln Lys Phe
 50                  55                  60
Gln Gly Arg Val Thr Met Thr Arg Asp Thr Pro Ile Ser Thr Ala Tyr
 65                  70                  75                  80
Met Asp Leu Ser Gly Leu Arg Ser Asp Asp Thr Ala Val Tyr Tyr Cys
                 85                  90                  95
Ala Arg Glu Thr Ile Gly Gly Trp Asn Ala Leu Asp Val Trp Gly Gln
            100                 105                 110
Gly Thr Leu Val Thr Val Ser Ser
        115                 120
```

<210> SEQ ID NO 15
<211> LENGTH: 327
<212> TYPE: DNA
<213> ORGANISM: Artificial Sequence
<220> FEATURE:
<223> OTHER INFORMATION: Synthetic Polypeptide

<400> SEQUENCE: 15

```
ctgcctgtgc tgactcagcc accctcagtg tcagtggccc aggacagaca ggccaggata    60
acctgtgggg gacacaagat tggaactaaa agtgtgcact ggtaccagca gaagccaggc   120
caggcccctg tactggtcgt ctatgatgat cgcgaccggc cctcagggat ccctgagcga   180
ttctctggct ccaactctgg gggcacggcc accctgacca tcagcagggt cgaagccggg   240
gatgaggccg actattactg tcaggtgtgg gatagtaata gtgatcatgt ggtgttcggc   300
ggagggacca agctgaccgt cctaagt                                       327
```

<210> SEQ ID NO 16
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 16

```
Met Pro Val Leu Thr Gln Pro Pro Ser Val Ser Val Ala Pro Gly Gln
1               5                   10                  15

Thr Ala Arg Ile Thr Cys Gly Gly His Lys Ile Gly Thr Lys Ser Val
            20                  25                  30

His Trp Tyr Gln Gln Lys Pro Gly Gln Ala Pro Val Leu Val Val Tyr
        35                  40                  45

Asp Asp Arg Asp Arg Pro Ser Gly Ile Pro Glu Arg Phe Ser Gly Ser
    50                  55                  60

Asn Ser Gly Gly Thr Ala Thr Leu Thr Ile Ser Arg Val Glu Ala Gly
65                  70                  75                  80

Asp Glu Ala Asp Tyr Tyr Cys Gln Val Trp Asp Ser Asn Ser Asp His
                85                  90                  95

Val Val Phe Gly Gly Gly Thr Lys Leu Thr Val Leu Ser
            100                 105
```

<210> SEQ ID NO 17
<211> LENGTH: 360
<212> TYPE: DNA
<213> ORGANISM: Artificial Sequence
<220> FEATURE:
<223> OTHER INFORMATION: Synthetic Polynucleotide

<400> SEQUENCE: 17

```
gaggtgcagc tggtgcagtc tggggctgat gtgaagaagc tggggcctc agtgaaggtc     60 tcctgcaagg cttctggata caccttcacc ggctactata tacactgggt gcgacaggcc   120
cctggacaag gcttgagtg gatgggatgg atcaacccta cagtggtgg cacaaactat    180 gcacagaagt ttcagggcag ggtcaccatg accagggaca cgtccatcag cacagcctac   240
atggagctga gcaggctgag atctgacgac acggccgtct attttgtgt gagagaggtg    300 aaagattact attattacat ggacgtctgg ggcagaggga ccacggtcac cgtctcctca   360
```

<210> SEQ ID NO 18
<211> LENGTH: 120
<212> TYPE: PRT
<213> ORGANISM: Artificial Sequence
<220> FEATURE:
<223> OTHER INFORMATION: Synthetic Polypeptide

<400> SEQUENCE: 18

```
Glu Val Gln Leu Val Gln Ser Gly Ala Asp Val Lys Lys Pro Gly Ala
1               5                   10                  15

Ser Val Lys Val Ser Cys Lys Ala Ser Gly Tyr Thr Phe Thr Gly Tyr
```

```
                    20                  25                  30
Tyr Ile His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Val Arg Glu Val Lys Asp Tyr Tyr Tyr Met Asp Val Trp Gly Arg
                100                 105                 110

Gly Thr Thr Val Thr Val Ser Ser
            115                 120

<210> SEQ ID NO 19
<211> LENGTH: 336
<212> TYPE: DNA
<213> ORGANISM: Artificial Sequence
<220> FEATURE:
<223> OTHER INFORMATION: Synthetic Polynucleotide

<400> SEQUENCE: 19
aattttatgc tgactcagcc ccactctgtg tcggaatctc cggggaagac ggttaccatc      60
tcgtgcaccc gcagcagcgg cagcattgcc agcaactccg tgcagtggta cctgcagcgc     120
ccgggcagtg cccccaccac tctgatcttt gacaataaac aaagaccgtc tggggtccct     180
gatcgcttct ctggctccat cgacagctcc tccaactctg cctccctcag catctctggg     240
ctgacgactg aggacgaggc tgactatttc tgtcagtctt atgatgacag tgagcaagtg     300
gtgttcggcg gagggaccaa gctgaccgtc ctaagt                               336

<210> SEQ ID NO 20
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 20

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Ser Val Gln Trp Tyr Leu Gln Arg Pro Gly Ser Ala Pro Thr Thr Leu
        35                  40                  45

Ile Phe Asp Asn Lys Gln Arg Pro Ser Gly Val Pro Asp Arg Phe Ser
    50                  55                  60

Gly Ser Ile Asp Ser Ser Ser Asn Ser Ala Ser Leu Ser Ile Ser Gly
65                  70                  75                  80

Leu Thr Thr Glu Asp Glu Ala Asp Tyr Phe Cys Gln Ser Tyr Asp Asp
                85                  90                  95

Ser Glu Gln Val Val Phe Gly Gly Gly Thr Lys Leu Thr Val Leu Ser
                100                 105                 110

<210> SEQ ID NO 21
<211> LENGTH: 363
<212> TYPE: DNA
<213> ORGANISM: Artificial Sequence
<220> FEATURE:
```

<223> OTHER INFORMATION: Synthetic Polynucleotide

<400> SEQUENCE: 21

```
gaggtgcagc tggtggagtc tggggctgag gtgaagaagc ctggggcctc agtgaaggtc    60
tcctgcaagg cttctggata caccttcacc ggctactata tgcactgggt gcgacaggcc   120
cctggacaag ggcttgagtg gttggggtgg gtcaaccctc acagtggtgg cacaaactat   180
gcacagaagt tcagggcag ggtcaccatg accagggaca cgtccatcag cacagcctac    240
atggagctga gcagactgag atctgacgac acggccgtat attactgtgc gagagagact   300
gatatctctg ctaattatca ctttgactac tggggccagg gcaccctggt caccgtctcc   360
tca                                                                 363
```

<210> SEQ ID NO 22
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 22

```
Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Leu
        35                  40                  45

Gly Trp Val Asn Pro His Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Asp Ile Ser Ala Asn Tyr His Phe Asp Tyr Trp Gly
            100                 105                 110

Gln Gly Thr Leu Val Thr Val Ser Ser
        115                 120
```

<210> SEQ ID NO 23
<211> LENGTH: 336
<212> TYPE: DNA
<213> ORGANISM: Artificial Sequence
<220> FEATURE:
<223> OTHER INFORMATION: Synthetic Polynucleotide

<400> SEQUENCE: 23

```
cagtctgccc tgactcagcc tgcctccgtg tctgggtctc ctggacagtc gatcaccatc    60
tcctgcactg gaaccagcag tgatgttggg agttataacg ctgtctcctg gtaccaacac   120
cacccaggca aagcccccaa actcatgatt tatgagtca gtaagcggcc ctcagggggtt    180
tctaatcggt tctctggctc caagtctggc aacacggcct ccctgacaat ctctgggctc   240
cgggctgagg acgaggctga ttattattgt gcaacatggg atgacagcct gaaaggtccg   300
gtgttcggcg gagggaccaa gctgaccgtc ctgggt                             336
```

<210> SEQ ID NO 24
<211> LENGTH: 113
<212> TYPE: PRT
<213> ORGANISM: Artificial Sequence

```
<220> FEATURE:
<223> OTHER INFORMATION: Synthetic Polypeptide

<400> SEQUENCE: 24

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
                20                  25                  30

Asn Ala Val Ser Trp Tyr Gln His Pro Gly Lys Ala Pro Lys Leu
            35                  40                  45

Met Ile Tyr Glu Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Arg Ala Glu Asp Glu Ala Asp Tyr Tyr Cys Ala Thr Trp Asp Asp Ser
                85                  90                  95

Leu Lys Gly Pro Val Phe Gly Gly Gly Thr Lys Leu Thr Val Leu Gly
            100                 105                 110

Glu

<210> SEQ ID NO 25
<211> LENGTH: 360
<212> TYPE: DNA
<213> ORGANISM: Artificial Sequence
<220> FEATURE:
<223> OTHER INFORMATION: Synthetic Polynucleotide

<400> SEQUENCE: 25
gaggtgcagc tggtgcagtc tggggctgag gtgaagaagc ctggggcctc agtgaaggtc     60
tcctgcaagg cttctggata caccttcacc ggctactata tgcactgggt gcgacaggcc   120
cctggacaag gcttgaatg gatgggatgg atcaaccta aaactggtga cacaaactat    180
gcacagaagt tcagggcag ggtcgccttg agcaggaca cgtccttcaa cacagcctac    240
atggacctga gcagcctcag atctgacgac acggccgtct attactgtgc gagagagggc    300
ctgtcgacca gcagtcccct tgactactgg ggccagggaa ccctggtcac cgtctcctca    360

<210> SEQ ID NO 26
<211> LENGTH: 120
<212> TYPE: PRT
<213> ORGANISM: Artificial Sequence
<220> FEATURE:
<223> OTHER INFORMATION: Synthetic Polypeptide

<400> SEQUENCE: 26

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Lys Thr Gly Asp Thr Asn Tyr Ala Gln Lys Phe
    50                  55                  60

Gln Gly Arg Val Ala Leu Ser Arg Asp Thr Ser Phe Asn Thr Ala Tyr
65                  70                  75                  80

Met Asp Leu Ser Ser Leu Arg Ser Asp Asp Thr Ala Val Tyr Tyr Cys
                85                  90                  95

Ala Arg Glu Gly Leu Ser Thr Ser Ser Pro Leu Asp Tyr Trp Gly Gln
```

```
                  100                 105                 110
Gly Thr Leu Val Thr Val Ser Ser
            115                 120

<210> SEQ ID NO 27
<211> LENGTH: 327
<212> TYPE: DNA
<213> ORGANISM: Artificial Sequence
<220> FEATURE:
<223> OTHER INFORMATION: Synthetic Polynucleotide

<400> SEQUENCE: 27
cagcctgggc tgactcagcc accctcagtg tcagtggccc caggacagtc ggccaagatt    60
acctgtggag aaaacgaact tgcaacaaat attgtacact ggtaccagca gaagccaggc   120
caggcccctg tgctggtcat ctatcatgat aacgaccggc cctcaggat ccctgagcga   180 ttctctggct ccaacgctgg gaacacggcc accctgacca tcagcagggt cgaagccggg   240
gatgaggccg acttttactg tcagctgtgg gatagtgcta gtgatcaagt ggtcttcggc   300
ggagggacca cgttgaccgt cctaggt                                       327

<210> SEQ ID NO 28
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 28

Gln Pro Gly Leu Thr Gln Pro Pro Ser Val Ser Val Ala Pro Gly Gln
1               5                   10                  15

Ser Ala Lys Ile Thr Cys Gly Glu Asn Glu Leu Ala Thr Asn Ile Val
            20                  25                  30

His Trp Tyr Gln Gln Lys Pro Gly Gln Ala Pro Val Leu Val Ile Tyr
        35                  40                  45

His Asp Asn Asp Arg Pro Ser Gly Ile Pro Glu Arg Phe Ser Gly Ser
    50                  55                  60

Asn Ala Gly Asn Thr Ala Thr Leu Thr Ile Ser Arg Val Glu Ala Gly
65                  70                  75                  80

Asp Glu Ala Asp Phe Tyr Cys Gln Leu Trp Asp Ser Ala Ser Asp Gln
                85                  90                  95

Val Val Phe Gly Gly Gly Thr Thr Leu Thr Val Leu Gly
            100                 105

<210> SEQ ID NO 29
<211> LENGTH: 363
<212> TYPE: DNA
<213> ORGANISM: Artificial Sequence
<220> FEATURE:
<223> OTHER INFORMATION: Synthetic Polynucleotide

<400> SEQUENCE: 29
gaggtgcagc tggtgcagtc agggggctgag gtgaagaggc ctggggcctc attgaaggtt    60
tcctgcaagg catctggata caccttcacc agccactata tacactgggt gcgacaggcc   120
cccggacaag ggcttgagtg gatgggatgg atcaacactg caatggtga cacaagatat    180 tcacagaggt tccagggcag agtcaccgtt accaggaca catccgcgag cacagtctac   240
atggaactga gcagcctgag atctgaagac acggccgtgt attactgtgc gagagagtct   300
agcagcagct ggtttgttgc ttttgatgtc tggggccaag ggaccacggt caccgtctcc   360
```

-continued tca                                                                                           363

<210> SEQ ID NO 30
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 30

Glu Val Gln Leu Val Gln Ser Gly Ala Glu Val Lys Arg Pro Gly Ala
1               5                   10                  15

Ser Leu Lys Val Ser Cys Lys Ala Ser Gly Tyr Thr Phe Thr Ser His
            20                  25                  30

Tyr Ile His Trp Val Arg Gln Ala Pro Gly Gln Gly Leu Glu Trp Met
        35                  40                  45

Gly Trp Ile Asn Thr Gly Asn Gly Asp Thr Arg Tyr Ser Gln Arg Phe
    50                  55                  60

Gln Gly Arg Val Thr Val Thr Arg Asp Thr Ser Ala Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ser Ser Ser Ser Trp Phe Val Ala Phe Asp Val Trp Gly
            100                 105                 110

Gln Gly Thr Thr Val Thr Val Ser Ser
        115                 120

<210> SEQ ID NO 31
<211> LENGTH: 327
<212> TYPE: DNA
<213> ORGANISM: Artificial Sequence
<220> FEATURE:
<223> OTHER INFORMATION: Synthetic Polynucleotide

<400> SEQUENCE: 31
cagcctgtgc tgactcagcc accctcggtg tcattggccc caggacagac ggccaggatt      60
acctgttcgg aaaagaacat tcgaagtaaa agagtgcact ggtaccagca gaagccaggc    120
caggcccctg tcctggtcat gtattctgat aacggccggc gctcagggat ccctgaccga    180 tttttctggct ccaactctgg gaacacggcc accctgacca tcaccagggt cgaagccggt    240
gatgagggcg acttttactg tcaggtgtgg gatccgatta ctgatcaggt ggttttcggc    300
ggagggacca gctgaccgt cctaggt                                          327

<210> SEQ ID NO 32
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 32

Gln Pro Val Leu Thr Gln Pro Pro Ser Val Ser Leu Ala Pro Gly Gln
1               5                   10                  15

Thr Ala Arg Ile Thr Cys Ser Glu Lys Asn Ile Arg Ser Lys Arg Val
            20                  25                  30

His Trp Tyr Gln Gln Lys Pro Gly Gln Ala Pro Val Leu Val Met Tyr
        35                  40                  45

Ser Asp Asn Gly Arg Arg Ser Gly Ile Pro Asp Arg Phe Ser Gly Ser

```
                  50                  55                  60

Asn Ser Gly Asn Thr Ala Thr Leu Thr Ile Thr Arg Val Glu Ala Gly
 65                  70                  75                  80

Asp Glu Gly Asp Phe Tyr Cys Gln Val Trp Asp Pro Ile Thr Asp Gln
                 85                  90                  95

Val Val Phe Gly Gly Gly Thr Lys Leu Thr Val Leu Gly
            100                 105

<210> SEQ ID NO 33
<211> LENGTH: 372
<212> TYPE: DNA
<213> ORGANISM: Artificial Sequence
<220> FEATURE:
<223> OTHER INFORMATION: Synthetic Polynucleotide

<400> SEQUENCE: 33
caggtgcagc tggtgcagtc tggggctgag gtgaagcagc ctgggtcctc agtgaaggtc      60
tcctgtaagg cttctggata caccttcacc ggctactata tgcactgggt gcgacaggcc    120
cctggagaag gcttgagtg ctgggatgg atcaaccctc acagtggtgg cacaaactat      180
gcacagaagt tccagggcag agtcacgatt accgcggaca atccacgag cacagcctac     240 atggagctga gcagcctgag atctgaggac acggctgtgt attactgtgc gagggagatt    300
gtggtggtga ctgctccggc tgctgcggct atggacgtct ggggccaagg caccctggtc    360
accgtctcct ca                                                       372

<210> SEQ ID NO 34
<211> LENGTH: 124
<212> TYPE: PRT
<213> ORGANISM: Artificial Sequence
<220> FEATURE:
<223> OTHER INFORMATION: Synthetic Polypeptide

<400> SEQUENCE: 34

Gln Val Gln Leu Val Gln Ser Gly Ala Glu Val Lys Gln Pro Gly Ser
  1               5                  10                  15

Ser Val Lys Val Ser Cys Lys Ala Ser Gly Tyr Thr Phe Thr Gly Tyr
                 20                  25                  30

Tyr Met His Trp Val Arg Gln Ala Pro Gly Glu Gly Leu Glu Trp Leu
             35                  40                  45

Gly Trp Ile Asn Pro His Ser Gly Gly Thr Asn Tyr Ala Gln Lys Phe
         50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Ile Val Val Val Thr Ala Pro Ala Ala Ala Met Asp
            100                 105                 110

Val Trp Gly Gln Gly Thr Leu Val Thr Val Ser Ser
        115                 120

<210> SEQ ID NO 35
<211> LENGTH: 333
<212> TYPE: DNA
<213> ORGANISM: Artificial Sequence
<220> FEATURE:
<223> OTHER INFORMATION: Synthetic Polypeptide

<400> SEQUENCE: 35
```

```
cagtctgtgc tgactcagcc accctccgcg tccgggtctc ctggacagtc agtcaccatc    60
tcctgcactg gaagcagcag tgacgttgct atttatgacc gtgtctcctg gtaccagcag   120
cccccaggca cagcccccaa actcattctt tatgatgtcc atgatcggcc ctcaggggtc   180
cctgatcgct tctctgggtc caagtctggc aacacggcct ccctgaccat ctctgggctc   240
caggctgagg acgaggctga ttattactgc agttcataca caaccagcgg cacttttgtc   300
ttcggaagtg ggaccaaggt caccgtccta ggt                                333
```

<210> SEQ ID NO 36
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 36

```
Gln Ser Val Leu Thr Gln Pro Pro Ser Ala Ser Gly Ser Pro Gly Gln
1               5                   10                  15

Ser Val Thr Ile Ser Cys Thr Gly Ser Ser Ser Asp Val Ala Ile Tyr
            20                  25                  30

Asp Arg Val Ser Trp Tyr Gln Gln Pro Pro Gly Thr Ala Pro Lys Leu
        35                  40                  45

Ile Leu Tyr Asp Val His Asp Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Thr Ser
                85                  90                  95

Gly Thr Phe Val Phe Gly Ser Gly Thr Lys Val Thr Val Leu Gly
            100                 105                 110
```

<210> SEQ ID NO 37
<211> LENGTH: 366
<212> TYPE: DNA
<213> ORGANISM: Artificial Sequence
<220> FEATURE:
<223> OTHER INFORMATION: Synthetic Polynucleotide

<400> SEQUENCE: 37

```
gaggtgcagc tggtgcagtc tggggctgag gtgaagaagc ctggggcctc agtgaacgtc    60
tcctgtaagg cttctggata caccttcacc ggctactata tgcactgggt gcgacaggcc   120
cctggacaag gcttgagtg gatgggatgg atcaacccca cagtggtgg cacaaactat     180 gcacagaagt tcagggcag ggtcaccgtg accacagaca cgtccaacag cacagcctac    240
atggagctga acaggctgaa atctgacgac acggccgtgt attattgtgc gagagagggg   300
tccggggacc ttgattcctt atacatggac gtctgggca aagggacaat ggtcaccgtc    360
tcttca                                                              366
```

<210> SEQ ID NO 38
<211> LENGTH: 324
<212> TYPE: DNA
<213> ORGANISM: Artificial Sequence
<220> FEATURE:
<223> OTHER INFORMATION: Synthetic Polynucleotide

<400> SEQUENCE: 38

```
tcctatgagc tgactcagcc accctcggtg tcagtggccc caggacagac ggccaggatt    60
```

```
acctgtgggg caaacaacat tggaagtaaa agtgtgcact ggtaccagca gaagccaggc      120
caggcccctg tgctggtcgt ctatgatgat agcgaccggc cctcagggat ccctgagcga      180
ttctctggct ccaactctgg gaacacggcc accctgacca tcacccaggt cgaagccggg      240
gatgaggccg actattactg tcagctatgg gatggtggga gtgatgtggt tttcggcgga      300
gggaccaagc tgaccgtcct aggt                                             324
```

<210> SEQ ID NO 39
<211> LENGTH: 122
<212> TYPE: PRT
<213> ORGANISM: Artificial Sequence
<220> FEATURE:
<223> OTHER INFORMATION: Synthetic Polypeptide

<400> SEQUENCE: 39

```
Glu Val Gln Leu Val Gln Ser Gly Ala Glu Val Lys Lys Pro Gly Ala
1               5                   10                  15

Ser Val Asn Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Val Thr Thr Asp Thr Ser Asn Ser Thr Ala Tyr
65                  70                  75                  80

Met Glu Leu Asn Arg Leu Lys Ser Asp Asp Thr Ala Val Tyr Tyr Cys
                85                  90                  95

Ala Arg Glu Gly Ser Gly Asp Leu Asp Ser Leu Tyr Met Asp Val Trp
            100                 105                 110

Gly Lys Gly Thr Met Val Thr Val Ser Ser
        115                 120
```

<210> SEQ ID NO 40
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 40

```
Ser Tyr Glu Leu Thr Gln Pro Pro Ser Val Ser Val Ala Pro Gly Gln
1               5                   10                  15

Thr Ala Arg Ile Thr Cys Gly Ala Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Thr Arg Val Glu Ala Gly
65                  70                  75                  80

Asp Glu Ala Asp Tyr Tyr Cys Gln Leu Trp Asp Gly Ser Asp Val
                85                  90                  95

Val Phe Gly Gly Gly Thr Lys Leu Thr Val Leu Gly
            100                 105
```

<210> SEQ ID NO 41
<211> LENGTH: 360
<212> TYPE: DNA

<213> ORGANISM: Artificial Sequence
<220> FEATURE:
<223> OTHER INFORMATION: Synthetic Polynucleotide

<400> SEQUENCE: 41

```
gaggtgcagc tggtggagtc tggggctgag gtgaagaagc ctggggcctc agtgaaggtc      60
tcctgcaaga cttctggata caccttcacc gaccactata tccactgggt gcgacaggcc     120
cctggacaag ggcttgagtg gatgggatgg atcaacccta gcagtggtgg cacagagtat     180
gcacagaagt ttcagggcag ggtcaccatg accagggaca cgcccattag cacggcctac     240
atggatctga gcgggctgag atctgacgac acggccgttt attactgtgc gagagagact     300
atcggtggct ggaacgcttt ggacgtctgg ggccaaggaa ccctggtcac cgtctcctca     360
```

<210> SEQ ID NO 42
<211> LENGTH: 120
<212> TYPE: PRT
<213> ORGANISM: Artificial Sequence
<220> FEATURE:
<223> OTHER INFORMATION: Synthetic Polypeptide

<400> SEQUENCE: 42

```
Glu Val Gln Leu Val Glu Ser Gly Ala Glu Val Lys Lys Pro Gly Ala
1               5                   10                  15

Ser Val Lys Val Ser Cys Lys Thr Ser Gly Tyr Thr Phe Thr Asp His
            20                  25                  30

Tyr Ile His Trp Val Arg Gln Ala Pro Gly Gln Gly Leu Glu Trp Met
        35                  40                  45

Gly Trp Ile Asn Pro Ser Ser Gly Gly Thr Glu Tyr Ala Gln Lys Phe
    50                  55                  60

Gln Gly Arg Val Thr Met Thr Arg Asp Thr Pro Ile Ser Thr Ala Tyr
65                  70                  75                  80

Met Asp Leu Ser Gly Leu Arg Ser Asp Asp Thr Ala Val Tyr Tyr Cys
                85                  90                  95

Ala Arg Glu Thr Ile Gly Gly Trp Asn Ala Leu Asp Val Trp Gly Gln
            100                 105                 110

Gly Thr Leu Val Thr Val Ser Ser
        115                 120
```

<210> SEQ ID NO 43
<211> LENGTH: 333
<212> TYPE: DNA
<213> ORGANISM: Artificial Sequence
<220> FEATURE:
<223> OTHER INFORMATION: Synthetic Polynucleotide

<400> SEQUENCE: 43

```
cagcctgtgc tgactcagcc accctcagcg tctgggaccc ccgggcagag ggtcaccatc      60
tcttgttctg gaagcagctc caacatcgga attaatactg taaactggta ccagcagctc     120
ccaagaacgc cccccaaact cctcatctat actaataatc agcggccctc aggggtccct     180
gaccgattct ctggctccaa gtctgacacc tcagcctccc tggccatcag tggcctccag     240
tctgaggatg aggctgatta ttactgtgca gcttgggatg acaccctgaa tggtccacta     300
ttcggcggag ggaccaaggt gaccgtccta ggt                                   333
```

<210> SEQ ID NO 44
<211> LENGTH: 111
<212> TYPE: PRT
<213> ORGANISM: Artificial Sequence

```
<220> FEATURE:
<223> OTHER INFORMATION: Synthetic Polypeptide

<400> SEQUENCE: 44

Gln Pro Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ile Asn
                20                  25                  30

Thr Val Asn Trp Tyr Gln Gln Leu Pro Arg Thr Pro Lys Leu Leu
            35                  40                  45

Ile Tyr Thr Asn Asn Gln Arg Pro Ser Gly Val Pro Asp Arg Phe Ser
    50                  55                  60

Gly Ser Lys Ser Asp Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Thr Leu
                85                  90                  95

Asn Gly Pro Leu Phe Gly Gly Gly Thr Lys Val Thr Val Leu Gly
            100                 105                 110

<210> SEQ ID NO 45
<211> LENGTH: 8
<212> TYPE: PRT
<213> ORGANISM: Artificial Sequence
<220> FEATURE:
<223> OTHER INFORMATION: Synthetic Oligopeptide

<400> SEQUENCE: 45

Gly Tyr Thr Phe Thr Asp His Tyr
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic Oligopeptide

<400> SEQUENCE: 46

Ile Asn Pro Ser Ser Gly Gly Thr
1               5

<210> SEQ ID NO 47
<211> LENGTH: 13
<212> TYPE: PRT
<213> ORGANISM: Artificial Sequence
<220> FEATURE:
<223> OTHER INFORMATION: Synthetic Oligopeptide

<400> SEQUENCE: 47

Ala Arg Glu Thr Ile Gly Gly Trp Asn Ala Leu Asp Val
1               5                   10

<210> SEQ ID NO 48
<211> LENGTH: 8
<212> TYPE: PRT
<213> ORGANISM: Artificial Sequence
<220> FEATURE:
<223> OTHER INFORMATION: Synthetic Oligopeptide

<400> SEQUENCE: 48

Ser Ser Asn Ile Gly Ile Asn Thr
1               5
```

```
<210> SEQ ID NO 49
<211> LENGTH: 3
<212> TYPE: PRT
<213> ORGANISM: Artificial Sequence
<220> FEATURE:
<223> OTHER INFORMATION: Synthetic Oligopeptide

<400> SEQUENCE: 49

Thr Asn Asn
1

<210> SEQ ID NO 50
<211> LENGTH: 11
<212> TYPE: PRT
<213> ORGANISM: Artificial Sequence
<220> FEATURE:
<223> OTHER INFORMATION: Synthetic Oligopeptide

<400> SEQUENCE: 50

Ala Ala Trp Asp Asp Thr Leu Asn Gly Pro Leu
1               5                   10

<210> SEQ ID NO 51
<211> LENGTH: 8
<212> TYPE: PRT
<213> ORGANISM: Artificial Sequence
<220> FEATURE:
<223> OTHER INFORMATION: Synthetic Oligopeptide

<400> SEQUENCE: 51

Gly Tyr Thr Phe Thr Gly Tyr Tyr
1               5

<210> SEQ ID NO 52
<211> LENGTH: 8
<212> TYPE: PRT
<213> ORGANISM: Artificial Sequence
<220> FEATURE:
<223> OTHER INFORMATION: Synthetic Oligopeptide

<400> SEQUENCE: 52

Ile Asn Pro Asn Ser Gly Gly Thr
1               5

<210> SEQ ID NO 53
<211> LENGTH: 12
<212> TYPE: PRT
<213> ORGANISM: Artificial Sequence
<220> FEATURE:
<223> OTHER INFORMATION: Synthetic Oligopeptide

<400> SEQUENCE: 53

Ala Arg Glu Gly Val His Ser Asp Ala Phe Asp Val
1               5                   10

<210> SEQ ID NO 54
<211> LENGTH: 6
<212> TYPE: PRT
<213> ORGANISM: Artificial Sequence
<220> FEATURE:
<223> OTHER INFORMATION: Synthetic Oligopeptide

<400> SEQUENCE: 54

Gln Ser Val Tyr Thr Asn
1               5

<210> SEQ ID NO 55
```

```
<211> LENGTH: 3
<212> TYPE: PRT
<213> ORGANISM: Artificial Sequence
<220> FEATURE:
<223> OTHER INFORMATION: Synthetic Oligopeptide

<400> SEQUENCE: 55

Gly Ala Ser
1

<210> SEQ ID NO 56
<211> LENGTH: 9
<212> TYPE: PRT
<213> ORGANISM: Artificial Sequence
<220> FEATURE:
<223> OTHER INFORMATION: 57

<400> SEQUENCE: 56

Gln Gln Tyr Gly Ser Ser His Phe Thr
1               5

<210> SEQ ID NO 57
<211> LENGTH: 8
<212> TYPE: PRT
<213> ORGANISM: Artificial Sequence
<220> FEATURE:
<223> OTHER INFORMATION: Synthetic Oligopeptide

<400> SEQUENCE: 57

Gly Tyr Thr Phe Thr Asp His Tyr
1               5

<210> SEQ ID NO 58
<211> LENGTH: 8
<212> TYPE: PRT
<213> ORGANISM: Artificial Sequence
<220> FEATURE:
<223> OTHER INFORMATION: Synthetic Oligopeptide

<400> SEQUENCE: 58

Ile Asn Pro Ser Ser Gly Gly Thr
1               5

<210> SEQ ID NO 59
<211> LENGTH: 13
<212> TYPE: PRT
<213> ORGANISM: Artificial Sequence
<220> FEATURE:
<223> OTHER INFORMATION: Synthetic Oligopeptide

<400> SEQUENCE: 59

Ala Arg Glu Thr Ile Gly Gly Trp Asn Ala Leu Asp Val
1               5                   10

<210> SEQ ID NO 60
<211> LENGTH: 8
<212> TYPE: PRT
<213> ORGANISM: Artificial Sequence
<220> FEATURE:
<223> OTHER INFORMATION: Synthetic Oligopeptide

<400> SEQUENCE: 60

Ser Ser Thr Ile Gly Arg His Ser
1               5

<210> SEQ ID NO 61
<211> LENGTH: 3
```

```
<212> TYPE: PRT
<213> ORGANISM: Artificial Sequence
<220> FEATURE:
<223> OTHER INFORMATION: Synthetic Oligopeptide

<400> SEQUENCE: 61

Ala Asn Asn
1

<210> SEQ ID NO 62
<211> LENGTH: 11
<212> TYPE: PRT
<213> ORGANISM: Artificial Sequence
<220> FEATURE:
<223> OTHER INFORMATION: Synthetic Oligopeptide

<400> SEQUENCE: 62

Ala Ala Trp Asp Asp Ser Leu Ser Gly Val Leu
1               5                   10

<210> SEQ ID NO 63
<211> LENGTH: 8
<212> TYPE: PRT
<213> ORGANISM: Artificial Sequence
<220> FEATURE:
<223> OTHER INFORMATION: Synthetic Oligopeptide

<400> SEQUENCE: 63

Gly Tyr Thr Phe Thr Asp His Tyr
1               5

<210> SEQ ID NO 64
<211> LENGTH: 7
<212> TYPE: PRT
<213> ORGANISM: Artificial Sequence
<220> FEATURE:
<223> OTHER INFORMATION: Synthetic Oligopeptide

<400> SEQUENCE: 64

Ile Asn Pro Ser Ser Gly Gly
1               5

<210> SEQ ID NO 65
<211> LENGTH: 13
<212> TYPE: PRT
<213> ORGANISM: Artificial Sequence
<220> FEATURE:
<223> OTHER INFORMATION: Synthetic Oligopeptide

<400> SEQUENCE: 65

Ala Arg Glu Thr Ile Gly Gly Trp Asn Ala Leu Asp Val
1               5                   10

<210> SEQ ID NO 66
<211> LENGTH: 6
<212> TYPE: PRT
<213> ORGANISM: Artificial Sequence
<220> FEATURE:
<223> OTHER INFORMATION: Synthetic Oligopeptide

<400> SEQUENCE: 66

Lys Ile Gly Thr Lys Ser
1               5

<210> SEQ ID NO 67
<211> LENGTH: 3
<212> TYPE: PRT
```

<213> ORGANISM: Artificial Sequence
<220> FEATURE:
<223> OTHER INFORMATION: Synthetic Oligopeptide

<400> SEQUENCE: 67

Asp Asp Arg
1

<210> SEQ ID NO 68
<211> LENGTH: 11
<212> TYPE: PRT
<213> ORGANISM: Artificial Sequence
<220> FEATURE:
<223> OTHER INFORMATION: Synthetic Oligopeptide

<400> SEQUENCE: 68

Gln Val Trp Asp Ser Asn Ser Asp His Val Val
1               5                   10

<210> SEQ ID NO 69
<211> LENGTH: 8
<212> TYPE: PRT
<213> ORGANISM: Artificial Sequence
<220> FEATURE:
<223> OTHER INFORMATION: Synthetic Oligopeptide

<400> SEQUENCE: 69

Gly Tyr Thr Phe Thr Gly Tyr Tyr
1               5

<210> SEQ ID NO 70
<211> LENGTH: 8
<212> TYPE: PRT
<213> ORGANISM: Artificial Sequence
<220> FEATURE:
<223> OTHER INFORMATION: Synthetic Oligopeptide

<400> SEQUENCE: 70

Ile Asn Pro Asn Ser Gly Gly Thr
1               5

<210> SEQ ID NO 71
<211> LENGTH: 13
<212> TYPE: PRT
<213> ORGANISM: Artificial Sequence
<220> FEATURE:
<223> OTHER INFORMATION: Synthetic Oligopeptide

<400> SEQUENCE: 71

Val Arg Glu Val Lys Asp Tyr Tyr Tyr Tyr Met Asp Val
1               5                   10

<210> SEQ ID NO 72
<211> LENGTH: 8
<212> TYPE: PRT
<213> ORGANISM: Artificial Sequence
<220> FEATURE:
<223> OTHER INFORMATION: Synthetic Oligopeptide

<400> SEQUENCE: 72

Ser Gly Ser Ile Ala Ser Asn Ser
1               5

<210> SEQ ID NO 73
<211> LENGTH: 3
<212> TYPE: PRT
<213> ORGANISM: Artificial Sequence

```
<220> FEATURE:
<223> OTHER INFORMATION: Synthetic Oligopeptide

<400> SEQUENCE: 73

Asp Asn Lys
1

<210> SEQ ID NO 74
<211> LENGTH: 10
<212> TYPE: PRT
<213> ORGANISM: Artificial Sequence
<220> FEATURE:
<223> OTHER INFORMATION: Synthetic Oligopeptide

<400> SEQUENCE: 74

Gln Ser Tyr Asp Asp Ser Glu Gln Val Val
1               5                   10

<210> SEQ ID NO 75
<211> LENGTH: 8
<212> TYPE: PRT
<213> ORGANISM: Artificial Sequence
<220> FEATURE:
<223> OTHER INFORMATION: Synthetic Oligopeptide

<400> SEQUENCE: 75

Gly Tyr Thr Phe Thr Gly Tyr Tyr
1               5

<210> SEQ ID NO 76
<211> LENGTH: 8
<212> TYPE: PRT
<213> ORGANISM: Artificial Sequence
<220> FEATURE:
<223> OTHER INFORMATION: Synthetic Oligopeptide

<400> SEQUENCE: 76

Val Asn Pro His Ser Gly Gly Thr
1               5

<210> SEQ ID NO 77
<211> LENGTH: 14
<212> TYPE: PRT
<213> ORGANISM: Artificial Sequence
<220> FEATURE:
<223> OTHER INFORMATION: Synthetic Oligopeptide

<400> SEQUENCE: 77

Ala Arg Glu Thr Asp Ile Ser Ala Asn Tyr His Phe Asp Tyr
1               5                   10

<210> SEQ ID NO 78
<211> LENGTH: 9
<212> TYPE: PRT
<213> ORGANISM: Artificial Sequence
<220> FEATURE:
<223> OTHER INFORMATION: Synthetic Oligopeptide

<400> SEQUENCE: 78

Ser Ser Asp Val Gly Ser Tyr Asn Ala
1               5

<210> SEQ ID NO 79
<211> LENGTH: 3
<212> TYPE: PRT
<213> ORGANISM: Artificial Sequence
<220> FEATURE:
```

<223> OTHER INFORMATION: Synthetic Oligopeptide

<400> SEQUENCE: 79

Glu Val Ser
1

<210> SEQ ID NO 80
<211> LENGTH: 11
<212> TYPE: PRT
<213> ORGANISM: Artificial Sequence
<220> FEATURE:
<223> OTHER INFORMATION: Synthetic Oligopeptide

<400> SEQUENCE: 80

Ala Thr Trp Asp Asp Ser Leu Lys Gly Pro Val
1               5                   10

<210> SEQ ID NO 81
<211> LENGTH: 8
<212> TYPE: PRT
<213> ORGANISM: Artificial Sequence
<220> FEATURE:
<223> OTHER INFORMATION: Synthetic Oligopeptide

<400> SEQUENCE: 81

Gly Tyr Thr Phe Thr Gly Tyr Tyr
1               5

<210> SEQ ID NO 82
<211> LENGTH: 8
<212> TYPE: PRT
<213> ORGANISM: Artificial Sequence
<220> FEATURE:
<223> OTHER INFORMATION: Synthetic Oligopeptide

<400> SEQUENCE: 82

Ile Asn Pro Lys Thr Gly Asp Thr
1               5

<210> SEQ ID NO 83
<211> LENGTH: 13
<212> TYPE: PRT
<213> ORGANISM: Artificial Sequence
<220> FEATURE:
<223> OTHER INFORMATION: Synthetic Oligopeptide

<400> SEQUENCE: 83

Ala Arg Glu Gly Leu Ser Thr Ser Ser Pro Leu Asp Tyr
1               5                   10

<210> SEQ ID NO 84
<211> LENGTH: 6
<212> TYPE: PRT
<213> ORGANISM: Artificial Sequence
<220> FEATURE:
<223> OTHER INFORMATION: Synthetic Oligopeptide

<400> SEQUENCE: 84

Glu Leu Ala Thr Asn Ile
1               5

<210> SEQ ID NO 85
<211> LENGTH: 3
<212> TYPE: PRT
<213> ORGANISM: Artificial Sequence
<220> FEATURE:
<223> OTHER INFORMATION: Synthetic Oligopeptide

<400> SEQUENCE: 85

His Asp Asn
1

<210> SEQ ID NO 86
<211> LENGTH: 11
<212> TYPE: PRT
<213> ORGANISM: Artificial Sequence
<220> FEATURE:
<223> OTHER INFORMATION: Synthetic Oligopeptide

<400> SEQUENCE: 86

Gln Leu Trp Asp Ser Ala Ser Asp Gln Val Val
1               5                   10

<210> SEQ ID NO 87
<211> LENGTH: 8
<212> TYPE: PRT
<213> ORGANISM: Artificial Sequence
<220> FEATURE:
<223> OTHER INFORMATION: Synthetic Oligopeptide

<400> SEQUENCE: 87

Gly Tyr Thr Phe Thr Ser His Tyr
1               5

<210> SEQ ID NO 88
<211> LENGTH: 8
<212> TYPE: PRT
<213> ORGANISM: Artificial Sequence
<220> FEATURE:
<223> OTHER INFORMATION: Synthetic Oligopeptide

<400> SEQUENCE: 88

Ile Asn Thr Gly Asn Gly Asp Thr
1               5

<210> SEQ ID NO 89
<211> LENGTH: 14
<212> TYPE: PRT
<213> ORGANISM: Artificial Sequence
<220> FEATURE:
<223> OTHER INFORMATION: Synthetic Oligopeptide

<400> SEQUENCE: 89

Ala Arg Glu Ser Ser Ser Ser Trp Phe Val Ala Phe Asp Val
1               5                   10

<210> SEQ ID NO 90
<211> LENGTH: 6
<212> TYPE: PRT
<213> ORGANISM: Artificial Sequence
<220> FEATURE:
<223> OTHER INFORMATION: Synthetic Oligopeptide

<400> SEQUENCE: 90

Asn Ile Arg Ser Lys Arg
1               5

<210> SEQ ID NO 91
<211> LENGTH: 3
<212> TYPE: PRT
<213> ORGANISM: Artificial Sequence
<220> FEATURE:
<223> OTHER INFORMATION: Synthetic Oligopeptide

```
<400> SEQUENCE: 91

Ser Asp Asn
1

<210> SEQ ID NO 92
<211> LENGTH: 11
<212> TYPE: PRT
<213> ORGANISM: Artificial Sequence
<220> FEATURE:
<223> OTHER INFORMATION: Synthetic Oligopeptide

<400> SEQUENCE: 92

Gln Val Trp Asp Pro Ile Thr Asp Gln Val Val
1               5                   10

<210> SEQ ID NO 93
<211> LENGTH: 8
<212> TYPE: PRT
<213> ORGANISM: Artificial Sequence
<220> FEATURE:
<223> OTHER INFORMATION: Synthetic Oligopeptide

<400> SEQUENCE: 93

Gly Tyr Thr Phe Thr Gly Tyr Tyr
1               5

<210> SEQ ID NO 94
<211> LENGTH: 8
<212> TYPE: PRT
<213> ORGANISM: Artificial Sequence
<220> FEATURE:
<223> OTHER INFORMATION: Synthetic Oligopeptide

<400> SEQUENCE: 94

Ile Asn Pro His Ser Gly Gly Thr
1               5

<210> SEQ ID NO 95
<211> LENGTH: 17
<212> TYPE: PRT
<213> ORGANISM: Artificial Sequence
<220> FEATURE:
<223> OTHER INFORMATION: Synthetic Oligopeptide

<400> SEQUENCE: 95

Ala Arg Glu Ile Val Val Val Thr Ala Pro Ala Ala Ala Ala Met Asp
1               5                   10                  15

Val

<210> SEQ ID NO 96
<211> LENGTH: 9
<212> TYPE: PRT
<213> ORGANISM: Artificial Sequence
<220> FEATURE:
<223> OTHER INFORMATION: Synthetic Oligopeptide

<400> SEQUENCE: 96

Ser Ser Asp Val Ala Ile Tyr Asp Arg
1               5

<210> SEQ ID NO 97
<211> LENGTH: 3
<212> TYPE: PRT
<213> ORGANISM: Artificial Sequence
<220> FEATURE:
<223> OTHER INFORMATION: Synthetic Oligopeptide
```

```
<400> SEQUENCE: 97

Asp Val His
1

<210> SEQ ID NO 98
<211> LENGTH: 10
<212> TYPE: PRT
<213> ORGANISM: Artificial Sequence
<220> FEATURE:
<223> OTHER INFORMATION: Synthetic Oligopeptide

<400> SEQUENCE: 98

Ser Ser Tyr Thr Thr Ser Gly Thr Phe Val
1               5                   10

<210> SEQ ID NO 99
<211> LENGTH: 8
<212> TYPE: PRT
<213> ORGANISM: Artificial Sequence
<220> FEATURE:
<223> OTHER INFORMATION: Synthetic Oligopeptide

<400> SEQUENCE: 99

Gly Tyr Thr Phe Thr Gly Tyr Tyr
1               5

<210> SEQ ID NO 100
<211> LENGTH: 8
<212> TYPE: PRT
<213> ORGANISM: Artificial Sequence
<220> FEATURE:
<223> OTHER INFORMATION: Synthetic Oligopeptide

<400> SEQUENCE: 100

Ile Asn Pro Asn Ser Gly Gly Thr
1               5

<210> SEQ ID NO 101
<211> LENGTH: 15
<212> TYPE: PRT
<213> ORGANISM: Artificial Sequence
<220> FEATURE:
<223> OTHER INFORMATION: Synthetic Oligopeptide

<400> SEQUENCE: 101

Ala Arg Glu Gly Ser Gly Asp Leu Asp Ser Leu Tyr Met Asp Val
1               5                   10                  15

<210> SEQ ID NO 102
<211> LENGTH: 6
<212> TYPE: PRT
<213> ORGANISM: Artificial Sequence
<220> FEATURE:
<223> OTHER INFORMATION: Synthetic Oligopeptide

<400> SEQUENCE: 102

Asn Ile Gly Ser Lys Ser
1               5

<210> SEQ ID NO 103
<211> LENGTH: 3
<212> TYPE: PRT
<213> ORGANISM: Artificial Sequence
<220> FEATURE:
<223> OTHER INFORMATION: Synthetic Oligopeptide
```

```
<400> SEQUENCE: 103

Asp Asp Ser
1

<210> SEQ ID NO 104
<211> LENGTH: 10
<212> TYPE: PRT
<213> ORGANISM: Artificial Sequence
<220> FEATURE:
<223> OTHER INFORMATION: Synthetic Oligopeptide

<400> SEQUENCE: 104

Gln Leu Trp Asp Gly Gly Ser Asp Val Val
1               5                   10

<210> SEQ ID NO 105
<211> LENGTH: 8
<212> TYPE: PRT
<213> ORGANISM: Artificial Sequence
<220> FEATURE:
<223> OTHER INFORMATION: Synthetic Oligopeptide

<400> SEQUENCE: 105

Gly Tyr Thr Phe Thr Asp His Tyr
1               5

<210> SEQ ID NO 106
<211> LENGTH: 8
<212> TYPE: PRT
<213> ORGANISM: Artificial Sequence
<220> FEATURE:
<223> OTHER INFORMATION: Synthetic Oligopeptide

<400> SEQUENCE: 106

Ile Asn Pro Ser Ser Gly Gly Thr
1               5

<210> SEQ ID NO 107
<211> LENGTH: 13
<212> TYPE: PRT
<213> ORGANISM: Artificial Sequence
<220> FEATURE:
<223> OTHER INFORMATION: Synthetic Oligopeptide

<400> SEQUENCE: 107

Ala Arg Glu Thr Ile Gly Gly Trp Asn Ala Leu Asp Val
1               5                   10

<210> SEQ ID NO 108
<211> LENGTH: 8
<212> TYPE: PRT
<213> ORGANISM: Artificial Sequence
<220> FEATURE:
<223> OTHER INFORMATION: Synthetic Oligopeptide

<400> SEQUENCE: 108

Ser Ser Asn Ile Gly Ile Asn Thr
1               5

<210> SEQ ID NO 109
<211> LENGTH: 3
<212> TYPE: PRT
<213> ORGANISM: Artificial Sequence
<220> FEATURE:
<223> OTHER INFORMATION: Synthetic Oligopeptide

<400> SEQUENCE: 109
```

```
Thr Asn Asn
1

<210> SEQ ID NO 110
<211> LENGTH: 11
<212> TYPE: PRT
<213> ORGANISM: Artificial Sequence
<220> FEATURE:
<223> OTHER INFORMATION: Synthetic Oligopeptide

<400> SEQUENCE: 110

Ala Ala Trp Asp Asp Thr Leu Asn Gly Pro Leu
1               5                   10
```

GLUCOCORTICOID-INDUCED TUMOR NECROSIS FACTOR RECEPTOR (GITR) ANTIBODIES AND METHODS OF USE THEREOF

RELATED APPLICATIONS

This application is a national stage entry of PCT Application No. PCT/US2015/054010, filed on Oct. 5, 2015, which claims priority to and the benefit of U.S. Provisional Application No. 62/059,458, filed on Oct. 3, 2014, the contents of each of which are incorporated by reference in their entirety.

FIELD OF THE INVENTION

This invention relates generally to anti-glucocorticoid-induced tumor necrosis factor receptor (GITR) antibodies as well as to methods for use thereof.

INCORPORATION-BY-REFERENCE OF SEQUENCE LISTING

The contents of the text file named "DFCI-093_001WO_ST25.txt", which was created on Oct. 5, 2015 and is 50 kilobytes in size, are hereby incorporated by reference in their entirety.

BACKGROUND OF THE INVENTION

The immune system must achieve a balance between effective responses to eliminate pathogenic entities (e.g. in cancer), while maintaining tolerance to prevent autoimmune disease. T cells serve a critical role in maintaining a balance between suppression of immune function, and active immune rejection. T regulatory cells (Tregs) are characterized by the expression of CD25+, CD4+, FOXp3+ and glucocorticoid-induced tumor necrosis factor-related receptor (GITR). Tregs suppress pathological immune responses, and ultimately maintain immune homeostasis by way of regulating immunological self-tolerance. The presence of Tregs suppresses the activity of activated, effector T cells which are responsible for eliminating various pathological entities.

Human epithelial malignancies have been associated with the presence of increased amounts of Tregs both in the circulation and within the tumor itself. The increased presence of suppressive Tregs in cancer patients, results in a suppression of conventional T cells, including effector cells, which in turn leads to a downregulation in IFN-γ production. Reduction of the presence or the activity of Tregs in in vivo cancer animal models has resulted in an increase in the amounts and activity of effector T cells, which is often followed by a decrease in size of the tumor and or alleviation of other cancer symptoms.

T cell activation results in an upregulation of GITR levels in both Tregs and effector T cells. Manners of modulating the activity of GITR, such that the Tregs immune suppressing function is reduced, and the activity of effector T cells is increased is an ongoing area of intense study. The GITR ligand, GITR-L, is expressed in a variety of cells including dendritic cells, macrophages and B cells. Previous studies have shown an association between increased anti-tumor immune activity following administration of exogenous GITR-L, or by alternate means of antagonizing GITR, in cancer models.

Given the increased presence, and the role that Tregs have in cancer, further attention to modulating the activity and presence of Tregs, via GITR, is paramount in further understanding and, ultimately, in the treatment of cancer. Therefore, there exists an urgent need for agents that can specifically bind and modulate the binding of GITR with its ligand, GITR-L, as a means to promote effector T cell activity and, as a result, anti-tumor activity.

SUMMARY OF THE INVENTION

In various aspects the invention provides an An isolated humanized monoclonal antibody or antigen-binding fragment thereof that binds to the human anti-glucocorticoid-induced tumor necrosis factor receptor (GITR). The antibody has a variable heavy chain region having the amino acid sequence of SEQ ID NO: 2, and a variable light chain region having the amino acid sequence of SEQ ID NO: 4; a variable heavy chain region having the amino acid sequence of SEQ ID NO: 6, and a variable light chain region having the amino acid sequence of SEQ ID NO: 8; a variable heavy chain region comprising the amino acid sequence of SEQ ID NO: 10, and a variable light chain region having the amino acid sequence of SEQ ID NO: 12; a variable heavy chain region having the amino acid sequence of SEQ ID NO: 14, and a variable light chain region having the amino acid sequence of SEQ ID NO: 16; a variable heavy chain region having the amino acid sequence of SEQ ID NO: 18, and a variable light chain region having the amino acid sequence of SEQ ID NO: 20; a variable heavy chain region having the amino acid sequence of SEQ ID NO: 22, and a variable light chain region having the amino acid sequence of SEQ ID NO: 24; a variable heavy chain region having the amino acid sequence of SEQ ID NO: 26, and a variable light chain region having the amino acid sequence of SEQ ID NO: 28; a variable heavy chain region having the amino acid sequence of SEQ ID NO: 30, and a variable light chain region having the amino acid sequence of SEQ ID NO: 32; a variable heavy chain region having the amino acid sequence of SEQ ID NO: 34, and a variable light chain region having the amino acid sequence of SEQ ID NO: 36; a variable heavy chain region having the amino acid sequence of SEQ ID NO: 38, and a variable light chain region having the amino acid sequence of SEQ ID NO: 40; or a variable heavy chain region having the amino acid sequence of SEQ ID NO: 42, and a variable light chain region having the amino acid sequence of SEQ ID NO: 44.

In a further aspect the invention provides an isolated humanized monoclonal antibody or antigen-binding fragment having a variable heavy chain complementarity determining region 1, 2, or 3 (VH-CDR) having the amino acid sequences of SEQ ID NO. 45, 46 or 47, respectively; and, a variable light chain complementarity determining region 1, 2 or 3 (VL-CDR) comprising the amino acid sequences of SEQ ID NO. 48, 49, or 50; a variable heavy chain complementarity determining region 1, 2, or 3 (VH-CDR) having the amino acid sequences of SEQ ID NO. 51, 52, or 53, respectively; and, a variable light chain complementarity determining region 1, 2 or 3 (VL-CDR) having the amino acid sequences of SEQ ID NO. 54, 55, or 56; a variable heavy chain complementarity determining region 1, 2, or 3 (VH-CDR) having the amino acid sequences of SEQ ID NO. 57, 58, or 59, respectively; and, a variable light chain complementarity determining region 1, 2 or 3 (VL-CDR) having the amino acid sequences of SEQ ID NO. 60, 61, or 62; a variable heavy chain complementarity determining region 1, 2, or 3 (VH-CDR) having the amino acid sequences of SEQ ID NO. 63, 64, or 65, respectively; and, a variable light chain complementarity determining region 1, 2 or 3 (VL-CDR) having the amino acid sequences of SEQ ID NO. 66, 67, or 68; a variable heavy chain complementarity determining region 1, 2, or 3 (VH-CDR) having the amino acid sequences of SEQ ID NO. 69, 70, or 71, respectively; and, a variable light chain complementarity determining region 1, 2 or 3 (VL-CDR) having the amino acid sequences of SEQ ID NO. 72, 73, or 74; a variable heavy chain complementarity determining region 1, 2, or 3 (VH-CDR) having the amino acid sequences of SEQ ID NO. 75, 76, or 77, respectively; and, a variable light chain complementarity determining region 1, 2 or 3 (VL-CDR) having the amino acid sequences of SEQ ID NO. 78, 79, or 80; a variable heavy chain complementarity determining region 1, 2, or 3 (VH-CDR) having the amino acid sequences of SEQ ID NO. 81, 82, or 83, respectively; and, a variable light chain complementarity determining region 1, 2 or 3 (VL-CDR) having the amino acid sequences of SEQ ID NO. 84, 85, or 86; a variable heavy chain complementarity determining region 1, 2, or 3 (VH-CDR) having the amino acid sequences of SEQ ID NO. 87, 88, or 89, respectively; and, a variable light chain complementarity determining region 1, 2 or 3 (VL-CDR) having the amino acid sequences of SEQ ID NO. 90, 91, or 92; a variable heavy chain complementarity determining region 1, 2, or 3 (VH-CDR) having the amino acid sequences of SEQ ID NO. 93, 94, or 95, respectively; and, a variable light chain complementarity determining region 1, 2 or 3 (VL-CDR) having the amino acid sequences of SEQ ID NO. 96, 97, or 98; a variable heavy chain complementarity determining region 1, 2, or 3 (VH-CDR) having the amino acid sequences of SEQ ID NO. 99, 100, or 101, respectively; and, a variable light chain complementarity determining region 1, 2 or 3 (VL-CDR) having the amino acid sequences of SEQ ID NO. 102, 103, or 104; or a variable heavy chain complementarity determining region 1, 2, or 3 (VH-CDR) having the amino acid sequences of SEQ ID NO. 105, 106, or 107, respectively; and, a variable light chain complementarity determining region 1, 2 or 3 (VL-CDR) having the amino acid sequences of SEQ ID NO. 108, 109, or 110.

The antibody is monovalent or bivalent. For example the antibody is a single chain antibody. The antibody has a binding affinity within the range of $10^{-5}$ M to $10^{-12}$ M. In some aspects the antibody has a IgG4 heavy chain constant region. In other aspects the antibody has an Fc region that contains mutations at amino acid positions 234 and 235. The mutations are for example, L234A and L235A.

In other aspects the invention includes a bi-specific antibody containing the human GITR antibody of the invention and an antibody that also binds to a tumor-associated antigen, a cytokine or a cell surface receptor.

Optionally the antibodies of the invention are s linked to a therapeutic agent, such as a toxin, a radiolabel, a siRNA, a small molecule, or a cytokine.

Also provide by the invention are cells producing the antibody according to the invention.

In various aspects the invention provides methods for depleting regulatory T-cells in a subject, by administering to a subject in need thereof a composition comprising an antibody according to the invention.

Other methods of the invention include augmenting an immune response to an antigen by administering to a subject in need thereof a composition comprising an antibody according to the invention. The antigen is a viral antigen, a bacterial antigen or a tumor associated antigen.

In various aspects administering an antibody according to the invention result in an increase in antigen specific T cell activity and/or an increase NK cell cytoxicity.

In some aspects the methods of the invention further includes administering to the subject IL-15.

In yet another aspect the invention includes methods of treating or alleviating a symptom of cancer by administering to a subject in need thereof a composition comprising an antibody according to the invention. The cancer is a cancer in which GITR or its ligand, GITR-L, is overexpressed. Optionally the subject is further administered a cytokine, such as IL-15 or a chemotherapeutic agent.

The invention further provides a nucleic acid having the nucleic acid sequence of SEQ ID NO: 1, 3, 5, 7, 9, 11, 13, 15, 17, 19, 21, 23, 25, 27, 29, 31, 33, 35, 37, 39, 41, 43.

In a further aspect the invention provides A nucleic acid encoding the polypeptide of SEQ ID NO: 2, 4, 6, 8, 10, 12, 14, 16, 18, 20, 22, 24, 26, 28, 30, 32, 34, 36, 38, 40, 42, 44 or polypeptide having the amino acid sequence of SEQ ID NO: 2, 4, 6, 8, 10, 12, 14, 16, 18, 20, 22, 24, 26, 28, 30, 32, 34, 36, 38, 40, 42, 44. Vectors containing the nucleic acids according to the invention are also provides. Also included in the invention are cell containing the vectors according to the invention.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

BRIEF DESCRIPTION OF THE DRAWINGS

FIG. 3 illustrates the kinetic characterization of an antibody-antigen interaction. GITR-C9 tag fusion protein was bound by mouse anti-C9 tag antibody and then immobilized onto mouse Fc biosensors. After a brief wash in buffer, the biosensors were exposed to a series of isotype-specific antibodies as noted in the legend. The $K_{on}$, $K_{off}$, and $K_D$ of each anti-GITR antibody were analyzed. $K_{on}$ ($M^{-1}$ $sec^{-1}$); $K_{off}$ ($sec^{-1}$); $K_D$ (M).

DETAILED DESCRIPTION

Figure 1:
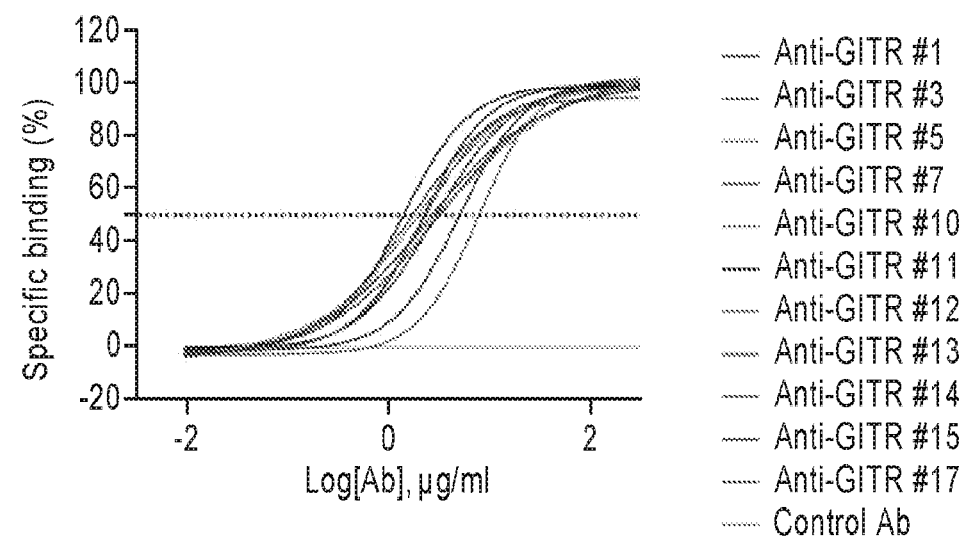
FIG. 1 is a graph showing the binding affinity of anti-GITR antibodies. The binding affinity of anti-GITR antibodies against GITR expressing 293T cells. GITR-expressed 293T cells were incubated with different concentrations of anti-GITR antibodies at 4° C. for one hour and then stained with FITC-labeled anti-human Fc antibody at 4° C. for another hour. Cells were further detected by flow cytometry and the half maximal effective concentrations ($EC_{50}$) of anti-GITR antibodies were measured by Prism software. These data suggested that the anti-GITR antibodies showed different binding activities on GITR.
Figure 2:
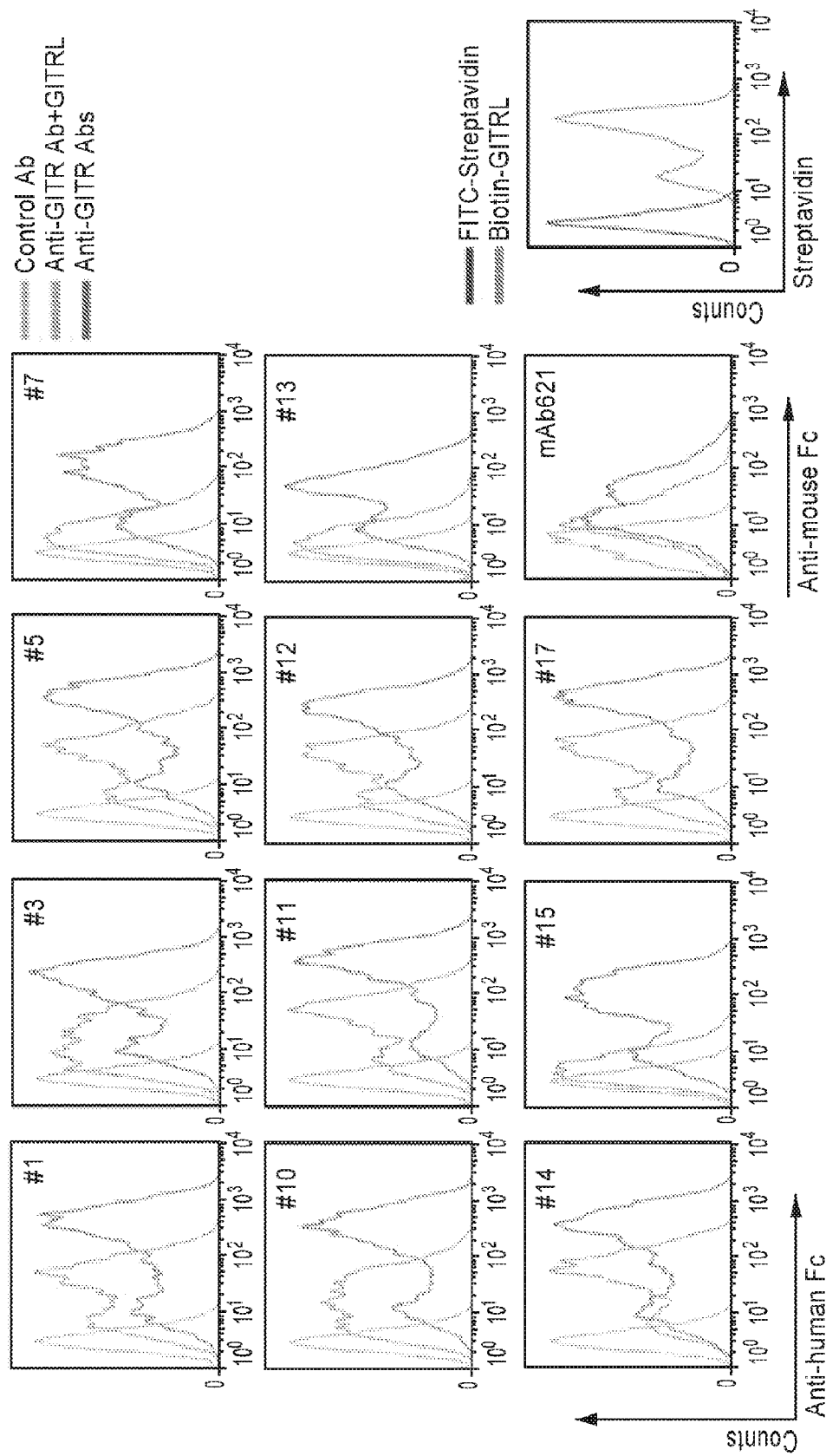
FIG. 2 is a series of graphs showing the competition activities of anti-GITR antibodies. GITR-expressed 293T cells were incubated with anti-GITR antibodies or MEM188 (commercial anti-GITR mAb) in the presence and absence of GITRL at 4° C. for one hour and then stained with FITC-labeled anti-human Fc antibody at 4° C. for another hour. Cells were further detected by flow cytometry and analyzed by FlowJo software. These result showed that all the anti-GITR antibody could block the interaction of GITRL and GITR, especially #7, 10, 13, and 15.
Figure 4:
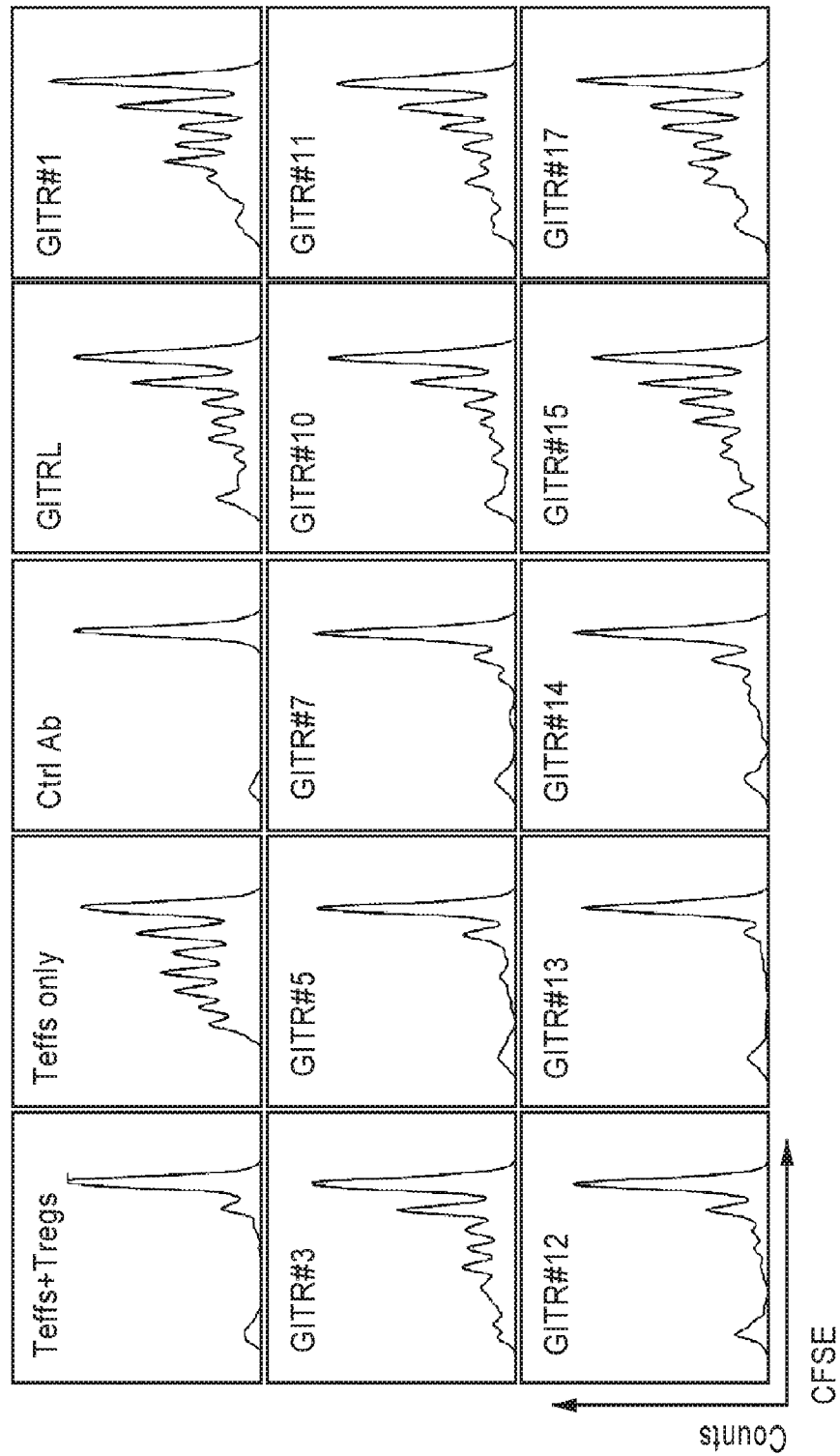
FIG. 4 is a series of graphs showing the bioactivities of anti-GITR antibodies on Teff and Treg co-culture. CFSE-labeled Teffs ($5 \times 10^4$) and unlabeled Tregs ($5 \times 10^3$) were co-incubated with 20 µg/ml PHA in 96-well plates for 5 days in the presence and absence of 20 µg/ml anti-GITR antibodies. The CFSE-labeled Teffs were harvested and CFSE intensity was analyzed by flow cytometry. Teffs were proliferated after 5-day incubation with PHA, but not in the Teff/Treg coculture. These data showed that #1, #3, #10, #11, #15, and #17 could help Teff proliferation by inhibiting Treg suppression function.
Figure 5:
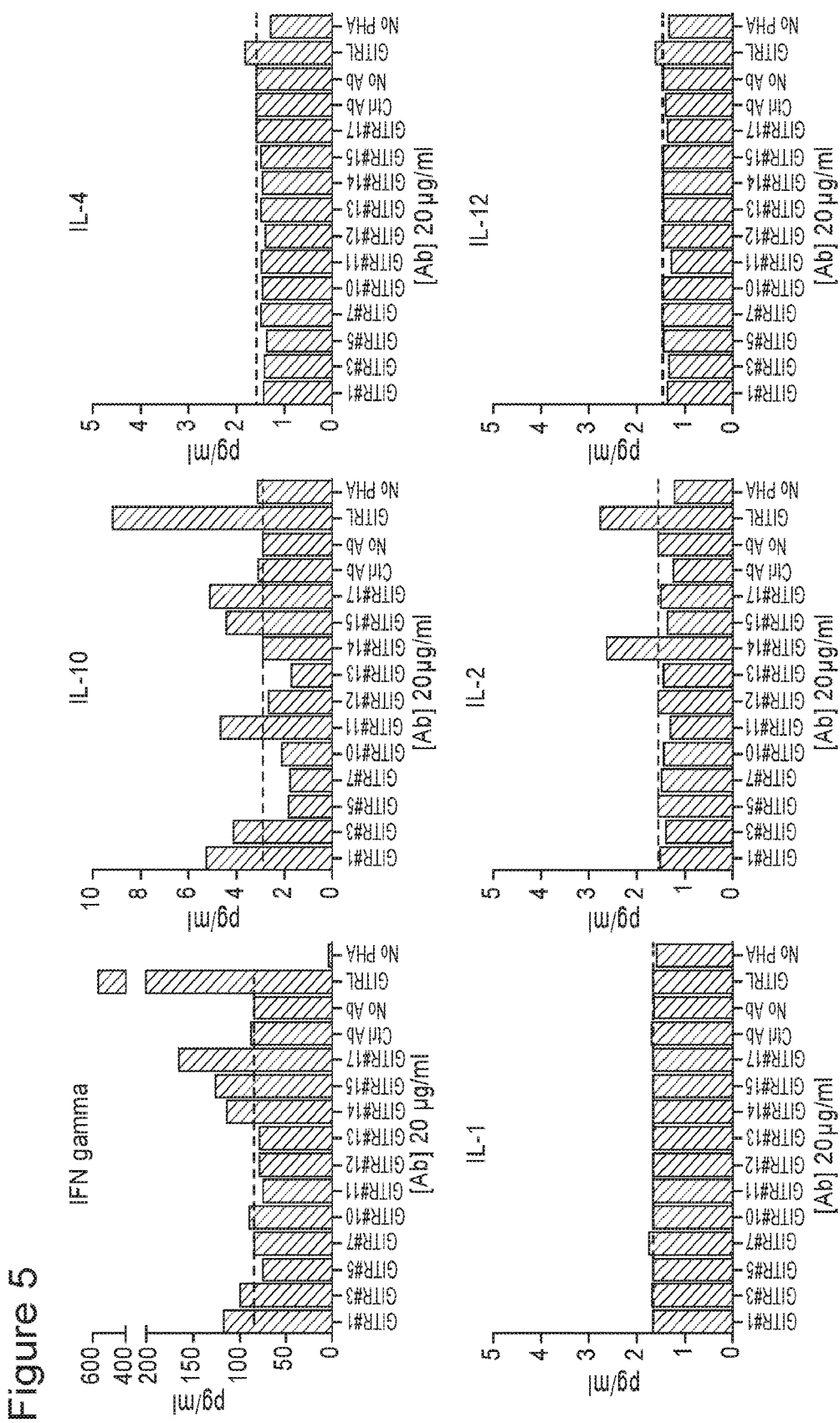
FIG. 5 is a series of charts illustrating the profile of cytokines stimulated by anti-GITR antibodies in a Teff and Treg co-culture. Cytokine production in the same cultures after 5 d at a Teff/Treg ratio of 10 was measured by MSD V-PLEX Kit. The data showed that #1, #3, #10, #14, #15, and #17 could induce IFN-gamma secretion and #1, #3, #11, #15, and #17 could induce IL-10 secretion. Taken together, #1, #3, #15, and #17 may have better activity as an agonist on GITR.

The present invention provides humanized monoclonal antibodies specific against glucocorticoid-induced tumor necrosis factor receptor, also known as GITR. The antibodies were identified through the use of a 27 billion human single-chain antibody (scFv) phage display library, by using GITR as the library selection target. These antibodies represent a new class of human monoclonal antibodies against GITR.

These anti-GITR human monoclonal antibodies are referred to herein as "huGITR antibodies".

There is documented evidence of an increase in the amounts of regulatory T-cells (Tregs) in cases of epithelial cancers. There is also evidence that GITR plays a key role in the dominant immunological self-tolerance maintained by Tregs. This connection between GITR expression on the Tregs, and the increase in Tregs during cancer, allows for an opportunity to target GITR activity as a means to promote enhanced effector T cell function. Specifically, this makes targeting GITR, a potential immunotherapeutic approach to cancer treatment.

Tregs express CD28, CD4, FOXP3, and GITR. The suppression of effector T cell activity is largely mediated by way of FOXP3 dimerization with activated T cell nuclear factor, NF-AT, which in turn results in the suppression of IFN-γ, IL-2 and IL-4. Increased GITR ligation by means of binding with its ligand has been shown to reduce the suppressive effects that Tregs have on activated T cells. Additionally, antibodies that directly target GITR have also been shown to reduce Treg suppressive function.

While GITR is expressed in both Tregs and in effector T cells, the amount of expression of GITR is drastically greater in the former. As such, GITR has been considered a good candidate target for the modulation of the suppressive function of Tregs in various diseases, including cancer. Murine models have indicated that stimulation of the GITR results in reduced Treg suppressive activity. Other studies have also indicated that antagonizing GITR activity results in a lessening of Treg recruitment to malignant cells. Combined, these data indicate GITR as a crucial receptor in the pathophysiology of cancer.

The present invention provides a human monoclonal antibody that specifically binds GITR proteins. Binding of the antibody of the present invention to GITR interrupts the GITR ligand's ability to bind to GITR. By a variety of mechanisms, the huGITR antibody reduces the suppressive function that Tregs have on effector cells. Administration of the huGITR antibody may result in Treg depletion, increased effector T cell (Teff) proliferation, increased antigen-specific T cell activity, and increased production of effector cytokines. In some instances, the huGITR antibody promotes or augments the antigen-specific immune response.

Accordingly, the huGITR antibodies of the invention are useful in modulating T-cell activity. In particular the huGITR antibodies can suppress Treg activity and stimulate Teff activity. Additionally, the huGITR antibodies of the invention increase NK– cell cytotoxicity and increase IFNγ secretion.

The huGITR antibody is monovalent or bivalent and comprises a single or double chain. Functionally, the binding affinity of the huGITR antibody is within the range of $10^{-5}$ M to $10^{-12}$ M. For example, the binding affinity of the huGITR antibody is from $10^{-6}$ M to $10^{-12}$ M, from $10^{-7}$ M to $10^{-12}$ M, from $10^{-8}$ M to $10^{-12}$ M, from $10^{-9}$ M to $10^{-12}$ M, from $10^{-5}$ M to $10^{-11}$ M, from $10^{-6}$ M to $10^{-11}$ M, from $10^{-7}$ M to $10^{-11}$ M, from $10^{-8}$ M to $10^{-11}$ M, from $10^{-9}$ M to $10^{-11}$ M, from $10^{-10}$ M to $10^{-11}$ M, from $10^{-5}$ M to $10^{-10}$ M from $10^{-6}$ M to $10^{-10}$ M, from $10^{-7}$ M to $10^{-10}$ M, from $10^{-8}$ M to $10^{-10}$ M, from $10^{-9}$ M to $10^{-10}$ M, from $10^{-5}$ M to $10^{-9}$ M, from $10^{-6}$ M to $10^{-9}$ M, from $10^{-7}$ M to $10^{-9}$ M, from $10^{-8}$ M to $10^{-9}$ M, from $10^{-5}$ M to $10^{-8}$ M, from $10^{-6}$ M to $10^{-8}$ M, from $10^{-7}$ M to $10^{-8}$ M, from $10^{-5}$ M to $10^{-7}$ M, from $10^{-6}$ M to $10^{-7}$ M or from $10^{-5}$ M to $10^{-6}$ M.

Furthermore, the antibody of the present invention comprises a therapeutic agent including, but not limited to, a toxin, a radiolabel, a siRNA, or a cytokine.

Eleven unique monoclonal huGITR antibodies were identified. These include mAb #1-81, 3-167, #5-139, #7-192, #10-116, #11-126, #12-46, #13-169, #14-182, #15-68, and #17-60. The variable region nucleic acid sequences and amino acid sequences are shown in Table 1A-11B. The amino acid sequences of the CDRs associated with the variable regions of these antibodies are shown in Table 12.

The nucleic acid and amino acid sequence of the monoclonal human GITR antibodies are provided below:

Table 1A. Ab #1-81 Variable Region nucleic acid sequences $V_H$ chain of Ab #1-81 VH (IGHV1-2*02)(SEQ ID NO: 1)
GAGGTGCAGCTGGTGGAGTCTGGGGCTGAGGTGAAGAAGCCTGGGGCCTC
AGTGAAGGTCTCCTGCAAGACTTCTGGATACACCTTCACCGACCACTATA
TCCACTGGGTGCGACAGGCCCCTGGACAAGGGCTTGAGTGGATGGGATGG
ATCAACCCTAGCAGTGGTGGCACAGAGTATGCACAGAAGTTTCAGGGCAG
GGTCACCATGACCAGGGACACGCCCATTAGCACGGCCTACATGGATCTGA
GCGGGCTGAGATCTGACGACACGGCCGTTTATTACTGTGCGAGAGAGACT
ATCGGTGGCTGGAACGCTTTGGACGTCTGGGGCCAAGGAACCCTGGTCAC
CGTCTCCTCA $V_L$ chain of Ab #1-81 (IGLV1-44*01)(SEQ ID NO: 3)
CAGCCTGTGCTGACTCAGCCACCCTCAGCGTCTGGGACCCCCGGGCAGAG
GGTCACCATCTCTTGTTCTGGAAGCAGCTCCAACATCGGAATTAATACTG
TAAACTGGTACCAGCAGCTCCCAAGAACGCCCCCCAAACTCCTCATCTAT
ACTAATAATCAGCGGCCCTCAGGGGTCCCTGACCGATTCTCTGGCTCCAA
GTCTGACACCTCAGCCTCCCTGGCCATCAGTGGCCTCCAGTCTGAGGATG
AGGCTGATTATTACTGTGCAGCTTGGGATGACACCCTGAATGGTCCACTA
TTCGGCGGAGGGACCAAGGTGACCGTCCTAGGT Table 1B. Ab #1-81 Variable Region amino acid sequences V<sub>H</sub> chain of Ab #1-81 VH (IGHV1-2*02)(SEQ ID NO: 2)
EVQLVESGAEVKKPGASVKVSCKTSGYTFTDHYTHWVRQAPGQGLEWMGW
INPSSGGTEYAQKFQGRVTMTRDTPISTAYMDLSGLRSDDTAVYYCARET
IGGWNALDVWGQGTLVTVSS V<sub>L</sub> chain of Ab #1-81 (IGLV1-44*01)(SEQ ID NO: 4)
QPVLTQPPSASGTPGQRVTISCSGSSSNIGINTVNWYQQLPRTPPKLLIY
TNNQRPSGVPDRFSGSKSDTSASLAISGLQSEDEADYYCAAWDDTLNGPL
FGGGTKVTVLG Table 2A. Ab #3-167 Variable Region nucleic acid sequences V<sub>H</sub> chain of Ab #3-167 VH (IGHV1-2*02)(SEQ ID NO: 5)
GAGGTGCAGCTGGTGCAGTCTGGGTCTGAGTTGAAGAAGCCTGGGGCCTC
AGTGAAGGTCTCCTGCAAGGCTTCTGGATACACCTTCACCGGCTACTATA
TGCACTGGGTGCGACAGGCCCCTGGACAAGGGCTTGAGTGGATGGGATGG
ATCAACCCTAACAGTGGTGGCACAAACTATGCACAGAAGTTTCAGGGCAG
GGTCACCGTGACCACAGACACGTCCACGAGCACAGCCTACATGGAGCTGA
GGAGCCTGAGATCTGACGACACGGCCGTCTATTACTGTGCGAGAGAGGGT
GTTCACTCGGATGCTTTTGATGTGTGGGGCCAAGGGACCACGGTCACCGT
CTCCTCA V<sub>L</sub> chain of Ab #3-167 VL (IGKV3-20*01)(SEQ ID NO: 7)
GAAACGACACTCACGCAGTCTCCAGCCACCCTGTCTGTGTCTCCAGGGGA
AAGGGCCACCCTCTCCTGCAGGGCCAGTCAGAGTGTTTACACCAACTTAG
CCTGGTACCAACAGAAACCTGGCCAGGCTCCCAGTCTCCTCATCTATGGT
GCATCCAGCCGGGCCACCGGCATCCCAGACAGATTCAGTGGCAGCGGGTC
TGGGACAGACTTCACTCTCACCATCAGCAGACTGGAGCCTGAAGATTTTG
CAGTGTATTACTGTCAGCAGTATGGTAGCTCACATTTCACTTTCGGCCCT
GGGACCAAAGTGGATATCAAA Table 2B. Ab #3-167 Variable Region amino acid sequences V<sub>H</sub> chain of Ab #3-167 VH (IGHV1-2*02)(SEQ ID NO: 6)
EVQLVQSGSELKKPGASVKVSCKASGYTFTGYYMHWVRQAPGQGLEWMGW
INPNSGGTNYAQKFQGRVTVTTDTSTSTAYMELRSLRSDDTAVYYCAREG
VHSDAFDVWGQGTTVTVSS V<sub>L</sub> chain of Ab 3-167 VL (IGKV3-20*01)(SEQ ID NO: 8)
ETTLTQSPATLSVSPGERATLSCRASQSVYTNLAWYQQKPGQAPSLLIYG
ASSRATGIPDRFSGSGSGTDFTLTISRLEPEDFAVYYCQQYGSSHETEGP
GTKVDIK Table 3A. Ab #5-139 Variable Region nucleic acid sequences V<sub>H</sub> chain of Ab #5-139 VH (IGHV1-2*02)(SEQ ID NO: 9)
GAGGTGCAGCTGGTGCAGTCTGGGGCTGAGGTGAAGAAGCCTGGGGCCTC
AGTGAAGGTCTCCTGCAAGACTTCTGGATACACCTTCACCGACCACTATA
TCCACTGGGTGCGACAGGCCCCTGGACAAGGGCTTGAGTGGATGGGATGG
ATCAACCCTAGCAGTGGTGGCACAGAGTATGCACAGAAGTTTCAGGGCAG
GGTCACCATGACCAGGGACACGCCCATTAGCACGGCCTACATGGATCTGA
GCGGGCTGAGATCTGACGACACGGCCGTTTATTACTGTGCGAGAGAGACT
ATCGGTGTGGCTGGAACGCTTTGGACGTCTGGGGCCAAGGGACCACGGTCAC
CGTCTCCTCA V<sub>L</sub> chain of Ab #5-139 VL (IGLV1-47*02)(SEQ ID NO: 11)
CAGTCTGTGCTGACTCAGCCACCCTCAGCGTCTGGGTCCCCGGGCAGAG
GGTCACCATGTCTTGCTCTGGAAGCAGCTCCACCATCGGGAGGCATTCTG
TAAACTGGTACCAGCAGCTCCCAGGAACGGCCCCCAAACTCCTCATCTAT
GCTAACAATCAGCGGCCCTCAGGGGTCCCTGGCCGATTCTCTGCCTCCAA
GTCTGACACCTCAGCCTCCCTGGCCATCAGTGGGCTCCGGTCCGAGGATG AGGCTAATTATTACTGTGCAGCGTGGGATGACAGTCTCAGTGGCGTGCTC
TTTGGCGGTGGGACCAAGGTGACCGTCCTAGGT Table 3B. Ab #5-139 Variable Region amino acid sequences V<sub>H</sub> chain of Ab #5-139 VH (IGHV1-2*02)(SEQ ID NO: 10)
EVQLVQSGAEVKKPGASVKVSCKTSGYTFTDHYIHWVRQAPGQGLEWMGW
INPSSGGTEYAQKFQGRVTMTRDTPISTAYMDLSGLRSDDTAVYYCARET
IGGWNALDVWGQGTTVTVSS V<sub>L</sub> chain of Ab #5-139 VL (IGLV1-47*02)(SEQ ID NO: 12)
QSVLTQPPSASGSPGQRVTMSCSGSSSTIGRHSVNWYQQLPGTAPKLLIY
ANNQRPSGVPGRESASKSDTSASLAISGLRSEDEANYYCAAWDDSLSGVL
FGGGTKVTVLG Table 4A. Ab #7-192 Variable Region nucleic acid sequences V<sub>H</sub> chain of Ab #7-192 VH (IGHV1-2*02)(SEQ ID NO: 13)
GAGGTGCAGCTGGTGGAGTCTGGGGCTGAGGTGAAGAAGCCTGGGGCCTC
AGTGAAGGTCTCCTGCAAGACTTCTGGATACACCTTCACCGACCACTATA
TCCACTGGGTGCGACAGGCCCCTGGACAAGGGCTTGAGTGGATGGGATGG
ATCAACCCTAGCAGTGGTGGCACAGAGTATGCACAGAAGTTTCAGGGCAG
GGTCACCATGACCAGGGACACGCCCATTAGCACGGCCTACATGGATCTGA
GCGGGCTGAGATCTGACGACACGGCCGTTTATTACTGTGCGAGAGAGACT
ATCGGTGGCTGGAACGCTTTGGACGTCTGGGGCCAAGGCACCCTGGTCAC
CGTCTCCTCA V<sub>L</sub> chain of Ab #7-192 VL (IGLV3-21*02)(SEQ ID NO: 15)
CTGCCTGTGCTGACTCAGCCACCCTCAGTGTCAGTGGCCCCAGGACAGAC
GGCCAGGATAACCTGTGGGGGACACAAGATTGGAACTAAAAGTGTGCACT
GGTACCAGCAGAAGCCAGGCCAGGCCCCTGTACTGGTCGTCTATGATGAT
CGCGACCGGCCCTCAGGGATCCCTGAGCGATTCTCTGGCTCCAACTCTGG
GGGCAGGCCACCCTGACCATCAGCAGGGTCGAAGCCGGGGATGAGGCCG
ACTATTACTGTCAGGTGTGGGATAGTAATAGTGATCATGTGGTGTTCGGC
GGAGGGACCAAGCTGACCGTCCTAAGT Table 4B. Ab #7-192 Variable Region amino acid sequences V<sub>H</sub> chain of Ab #7-192 VH (IGHV1-2*02)(SEQ ID NO: 14)
EVQLVESGAEVKKPGASVKVSCKTSGYTFTDHYIHWVRQAPGQGLEWMGW
INPSSGGTEYAQKFQGRVTMTRDTPISTAYMDLSGLRSDDTAVYYCARET
IGGWNALDVWGQGTLVTVSS V<sub>L</sub> chain of Ab #7-192 VL (IGLV3-21*02)(SEQ ID NO: 16)
MPVLTQPPSVSVAPGQTARITCGGHKIGTKSVHWYQQKPGQAPVLVVYDD
RDRPSGIPERFSGSNSGGTATLTISRVEAGDEADYYCQVWDSNSDHVVFG
GGTKLTVLS Table 5A. Ab #10-116 Variable Region nucleic acid sequences V<sub>H</sub> chain of Ab #10-116 VH (IGHV1-2*02)(SEQ ID NO: 17)
GAGGTGCAGCTGGTGCAGTCTGGGGCTGATGTGAAGAAGCCTGGGGCCTC
AGTGAAGGTCTCCTGCAAGGCTTCTGGATACACCTTCACCGGCTACTATA
TACACTGGGTGCGACAGGCCCCTGGACAAGGGCTTGAGTGGATGGGATGG
ATCAACCCTAACAGTGGTGGCACAAACTATGCACAGAAGTTTCAGGGCAG
GGTCACCATGACCAGGGACACGCCCATCACACAGGCCTACATGGAGCTGA
GCAGGCTGAGATCTGACGACACGGCCGTCTATTTTTGTGTGAGAGAGGTG
AAAGATTACTATTATTACATGGACGTCTGGGGCAGAGGGACCACGGTCAC
CGTCTCCTCA

$V_L$ chain of Ab #10-116 VL (IGLV6-57*01) (SEQ ID NO: 19)
AATTTTATGCTGACTCAGCCCCACTCTGTGTCGGAATCTCCGGGGAAGAC
GGTTACCATCTCGTGCACCCGCAGCAGCGGCAGCATTGCCAGCAACTCCG
TGCAGTGGTACCTGCAGCGCCCGGGCAGTGCCCCCACCACTCTGATCTTT
GACAATAAACAAAGACCGTCTGGGGTCCCTGATCGCTTCTCTGGCTCCAT
CGACAGCTCCTCCAACTCTGCCTCCCTCAGCATCTCTGGGCTGACGACTG
AGGACGAGGCTGACTATTTCTGTCAGTCTTATGATGACAGTGAGCAAGTG
GTGTTCGGCGGAGGGACCAAGCTGACCGTCCTAAGT

Table 5B. Ab #10-116 Variable Region amino acid sequences $V_H$ chain of Ab #10-116 VH (IGHV1-2*02) (SEQ ID NO: 18)
EVQLVQSGADVKKPGASVKVSCKASGYTFTGYYIHWVRQAPGQGLEWMGW
INPNSGGTNYAQKFQGRVTMTRDTSISTAYMELSRLRSDDTAVYFCVREV
KDYYYMDVWGRGTTVTVSS $V_L$ chain of Ab #10-116 VL (IGLV6-57*01) (SEQ ID NO: 20)
NFMLTQPHSVSESPGKTVTISCTRSSGSIASNSVQWYLQRPGSAPTTLIF
DNKQRPSGVPDRFSGSIDSSSNSASLSISGLTTEDEADYFCQSYDDSEQV
VFGGGTKLTVLS

Table 6A. #11-126 Variable Region nucleic acid sequences $V_H$ chain of #11-126 VH (IGHV1-2*02) (SEQ ID NO: 21)
GAGGTGCAGCTGGTGGAGTCTGGGGCTGAGGTGAAGAAGCCTGGGGCCTC
AGTGAAGGTCTCCTGCAAGGCTTCTGGATACACCTTCACCGGCTACTATA
TGCACTGGGTGCGACAGGCCCCTGGACAAGGGCTTGAGTGGTTGGGGTGG
GTCAACCCTCACAGTGGTGGCACAAACTATGCACAGAAGTTTCAGGGCAG
GGTCACCATGACCAGGGACACGTCCATCAGCACAGCCTACATGGAGCTGA
GCAGACTGAGATCTGACGACACGGCCGTATATTACTGTGCGAGAGAGACT
GATATCTCTGCTAATTATCACTTTGACTACTGGGGCCAGGGCACCCTGGT
CACCGTCTCCTCA $V_L$ chain of #11-126 VL (IGLV2-23*02) (SEQ ID NO:23)
CAGTCTGCCCTGACTCAGCCTGCCTCCGTGTCTGGGTCTCCTGGACAGTC
GATCACCATCTCCTGCACTGGAACCAGCAGTGATGTTGGGAGTTATAACG
CTGTCTCCTGGTACCAACACCACCCAGGCAAAGCCCCCAAACTCATGATT
TATGAGGTCAGTAAGCGGCCCTCAGGGGTTTCTAATCGGTTCTCTGGCTC
CAAGTCTGGCAACACGGCCTCCCTGACAATCTCTGGGCTCCGGGCTGAGG
ACGAGGCTGATTATTATTGTGCAACATGGGATGACAGCCTGAAAGGTCCG
GTGTTCGGCGGAGGGACCAAGCTGACCGTCCTGGGT

Table 6B. #11-126 Variable Region amino acid sequences $V_H$ chain of #11-126 VH (IGHV1-2*02) (SEQ ID NO: 22)
EVQLVESGAEVKKPGASVKVSCKASGYTFTGYYMHWVRQAPGQGLEWLGW
VNPHSGGTNYAQKFQGRVTMTRDTSISTAYMELSRLRSDDTAVYYCARET
DISANYHFDYWGQGTLVTVSS $V_L$ chain of #11-126 VL (IGLV2-23*02) (SEQ ID NO: 24)
QSALTQPASVSGSPGQSITISCTGTSSDVGSYNAVSWYQHHPGKAPKLMI
YEVSKRPSGVSNRFSGSKSGNTASLTISGLRAEDEADYYCATWDDSLKGP
VFGGGTKLTVLG

Table 7A. #12-46 Variable Region nucleic acid sequences $V_H$ chain of #12-46 VH (IGHV1-2*02) (SEQ ID NO: 25)
GAGGTGCAGCTGGTGCAGTCTGGGGCTGAGGTGAAGAAGCCTGGGGCCTC
AGTGAAGGTCTCCTGCAAGGCTTCTGGATACACCTTCACCGGCTACTATA
TGCACTGGGTGCGACAGGCCCCTGGACAAGGGCTTGAATGGATGGGATGG
ATCAACCCTAAAACTGGTGACACAAACTATGCACAGAAGTTTCAGGGCAG
GGTCGCCTTGAGCAGGGACACGTCCTTCAACACAGCCTACATGGACCTGA
GCAGCCTCAGATCTGACGACACGGCCGTCTATTACTGTGCGAGAGAGGGC
CTGTCGACCAGCAGTCCCCTTGACTACTGGGGCCAGGGAACCCTGGTCAC
CGTCTCCTCA $V_L$ chain of #12-46 VL (IGLV3-21*01) (SEQ ID NO: 27)
CAGCCTGGGCTGACTCAGCCACCCTCAGTGTCAGTGGCCCCAGGACAGTC
GGCCAAGATTACCTGTGGAGAAAACGAACTTGCAACAAATATTGTACACT
GGTACCAGCAGAAGCCAGGCCAGGCCCCTGTGCTGGTCATCTATCATGAT
AACGACCGGCCCTCAGGGATCCCTGAGCGATTCTCTGGCTCCAACGCTGG
GAACACGGCCACCCTGACCATCAGCAGGGTCGAAGCCGGGGATGAGGCCG
ACTTTTACTGTCAGCTGTGGGATAGTGCTAGTGATCAAGTGGTCTTCGGC
GGAGGGACCACGTTGACCGTCCTAGGT

Table 7B. #12-46 Variable Region amino acid sequences $V_H$ chain of #12-46 VH (IGHV1-2*02) (SEQ ID NO: 26)
EVQLVQSGAEVKKPGASVKVSCKASGYTFTGYYMHWVRQAPGQGLEWMGW
INPKTGDTNYAQKFQGRVALSRDTSFNTAYMDLSSLRSDDTAVYYCAREG
LSTSSPLDYWGQGTLVTVSS $V_L$ chain of #12-46 VL (IGLV3-21*01) (SEQ ID NO: 28)
QPGLTQPPSVSVAPGQSAKITCGENELATNIVHWYQQKPGQAPVLVIYHD
NDRPSGIPERFSGSNAGNTATLTISRVEAGDEADFYCQLWDSASDQVVFG
GGTTLTVLG

Table 8A. #13-169 Variable Region nucleic acid sequences $V_H$ chain of #13-169 VH (IGHV1-3*01) (SEQ ID NO: 29)
GAGGTGCAGCTGGTGCAGTCAGGGGCTGAGGTGAAGAGGCCTGGGGCCTC
ATTGAAGGTTTCCTGCAAGGCATCTGGATACACCTTCACCAGCCACTATA
TACACTGGGTGCGACAGGCCCCCGGACAAGGGCTTGAGTGGATGGGATGG
ATCAACACTGGCAATGGTGACACAAGATATTCACAGAGGTTCCAGGGCAG
AGTCACCGTTACCAGGGACACATCCGCGAGCACAGTCTACATGGAACTGA
GCAGCCTGAGATCTGAAGACACGGCCGTGTATTACTGTGCGAGAGAGTCT
AGCAGCAGCTGGTTTGTTGCTTTTGATGTCTGGGGCCAAGGGACCACGGT
CACCGTCTCCTCA $V_L$ chain of #13-169 VL (IGLV3-21*02) (SEQ ID NO: 31)
CAGCCTGTGCTGACTCAGCCACCCTCGGTGTCATTGGCCCCAGGACAGAC
GGCCAGGATTACCTGTTCGGAAAAGAACATTCGAAGTAAAAGAGTGCACT
GGTACCAGCAGAAGCCAGGCCAGGCCCCTGTCCTGGTCATGTATTCTGAT
AACGGCCGGCGCTCAGGGATCCCTGACCGATTTTCTGGCTCCAACTCTGG
GAACACGGCCACCCTGACCATCACCAGGGTCGAAGCCGGTGATGAGGCCG
ACTTTTACTGTCAGGTGTGGGATCCGATTACTGATCAGGTGGTTTTCGGC
GGAGGGACCAAGCTGACCGTCCTAGGT

Table 8B. #13-169 Variable Region amino acid sequences $V_H$ chain of #13-169 VH (IGHV1-3*01) (SEQ ID NO: 30)
EVQLVQSGAEVKRPGASLKVSCKASGYTFTSHYIHWVRQAPGQGLEWMGW
INTGNGDTRYSQRFQGRVTVTRDTSASTVYMELSSLRSEDTAVYYCARES
SSSWFVAFDVWGQGTTVTVSS $V_L$ chain of #13-169 VL (IGLV3-21*02) (SEQ ID NO: 32)
QPVLTQPPSVSLAPGQTARITCSEKNIRSKRVHWYQQKPGQAPVLVMYSD
NGRRSGIPDRFSGSNSGNTATLTITRVEAGDEGDFYCQVWDPITDQVVFG
GGTKLTVLG

Table 9A. #14-182 Variable Region nucleic acid sequences $V_H$ chain of #14-182 VH (IGHV1-2*02) (SEQ ID NO: 33)
CAGGTGCAGCTGGTGCAGTCTGGGGCTGAGGTGAAGCAGCCTGGGTCCTC
AGTGAAGGTCTCCTGTAAGGCTTCTGGATACACCTTCACCGGCTACTATA
TGCACTGGGTGCGACAGGCCCCTGGAGAAGGGCTTGAGTGGCTGGGATGG
ATCAACCCTCACAGTGGTGGCACAAACTATGCACAGAAGTTCCAGGGCAG
AGTCACGATTACCGCGGACAAATCCACGAGCACAGCCTACATGGAGCTGA
GCAGCCTGAGATCTGAGGACACGGCTGTGTATTACTGTGCGAGGGAGATT

GTGGTGGTGACTGCTCCGGCTGCTGCGGCTATGGACGTCTGGGGCCAAGG
CACCCTGGTCACCGTCTCCTCA

V_L chain of #14-182 VL (IGLV2-18*02)(SEQ ID
NO: 35)
CAGTCTGTGCTGACTCAGCCACCCTCCGCGTCCGGGTCTCCTGGACAGTC
AGTCACCATCTCCTGCACTGGAAGCAGCAGTGACGTTGCTATTTATGACC
GTGTCTCCTGGTACCAGCAGCCCCCAGGCACAGCCCCCAAACTCATTCTT
TATGATGTCCATGATCGGCCCTCAGGGGTCCCTGATCGCTTCTCTGGGTC
CAAGTCTGGCAACACGGCCTCCCTGACCATCTCTGGGCTCCAGGCTGAGG
ACGAGGCTGATTATTACTGCAGTTCATACACAACCAGCGGCACTTTTGTC
TTCGGAAGTGGGACCAAGGTCACCGTCCTAGGT Table 9B. #14-182 Variable Region amino acid
sequences V_H chain of #14-182 VH (IGHV1-2*02)(SEQ ID NO: 34)
QVQLVQSGAEVKQPGSSVKVSCKASGYTFTGYYMHWVRQAPGEGLEWLGW
INPHSGGTNYAQKFQGRVTITADKSTSTAYMELSSLRSEDTAVYYCAREI
VVVTAPAAAMDVWGQGTLVTVSS V_L chain of #14-182 VL (IGLV2-18*02)(SEQ ID
NO: 36)
QSVLTQPPSASGSPGQSVTISCTGSSSDVAIYDRVSWYQQPPGTAPKLIL
YDVHDRPSGVPDRFSGSKSGNTASLTISGLQAEDEADYYCSSYTTSGTFV
FGSGTKVTVLG

TABLE 10A

15-68 Variable Region nucleic acid sequences

V_H chain of #15-68 VH (IGHV1-2*02) (SEQ ID NO: 37)
GAGGTGCAGCTGGTGCAGTCTGGGGCTGAGGTGAAGAAGCCTGGGGCCTCA

GTGAACGTCTCCTGTAAGGCTTCTGGATACACCTTCACCGGCTACTATATG

CACTGGGTGCGACAGGCCCCTGGACAAGGGCTTGAGTGGATGGGATGGATC

AACCCCAACAGTGGTGGCACAAACTATGCACAGAAGTTTCAGGGCAGGGTC

ACCGTGACCACAGACACGTCCAACAGCACAGCCTACATGGAGCTGAACAGG

CTGAAATCTGACGACACGGCCGTGTATTATTGTGCGAGAGAGGGGTCCGGG

GACCTTGATTCCTTATACATGGACGTCTGGGGCAAAGGGACAATGGTCACC

GTCTCTTCA

V_L chain of #15-68 VL (IGLV3-21*02) (SEQ ID NO: 38)
TCCTATGAGCTGACTCAGCCACCCTCGGTGTCAGTGGCCCCAGGACAGAG

GCCAGGATTACCTGTGGGGCAAACAACATTGGAAGTAAAAGTGTGCACTGG

TACCAGCAGAAGCCAGGCCAGGCCCCTGTGCTGGTCGTCTATGATGATAGC

GACCGGCCCTCAGGGATCCCTGAGCGATTCTCTGGCTCCAACTCTGGGAAC

ACGGCCACCCTGACCATCACCAGGGTCGAAGCCGGGGATGAGGCCGACTAT

TACTGTCAGCTATGGGATGGTGGGAGTGATGTGGTTTTCGGCGGAGGGACC

AAGCTGACCGTCCTAGGT

TABLE 10B

15-68 Variable Region amino acid sequences

V_H chain of #15-68 VH (IGHV1-2*02) (SEQ ID NO: 39)
EVQLVQSGAEVKKPGASVNVSCKASGYTFTGYYMHWVRQAPGQGLEWMGW

INPNSGGTNYAQKFQGRVTVTTDTSNSTAYMELNRLKSDDTAVYYCAREG

SGDLDSLYMDVWGKGTMVTVSS

TABLE 10B-continued

15-68 Variable Region amino acid sequences

V_L chain of #15-68 VL (IGLV3-21*02) (SEQ ID NO: 40)
SYELTQPPSVSVAPGQTARITCGANNIGSKSVHWYQQKPGQAPVLVVYDD

SDRPSGIPERFSGSNSGNTATLTITRVEAGDEADYYCQLWDGGSDVVFGG

GTKLTVLG

Table 11A. #17-190 Variable Region nucleic acid
sequences

V_H chain of #17-190 VH (IGHV1-2*02)(SEQ ID NO: 41)
GAGGTGCAGCTGGTGCAGTCTGGGGCTGAGGTGAAGAAGCCTGGGGCCTC
AGTGAAGGTCTCCTGCAAGACTTCTGGATACACCTTCACCGACCACTATA
TCCACTGGGTGCGACAGGCCCCTGGACAAGGGCTTGAGTGGATGGGATGG
ATCAACCCTAGCAGTGGTGGCACAGAGTATGCACAGAAGTTTCAGGGCAG
GGTCACCATGACCAGGGACACGCCCATTAGCACGGCCTACATGGATCTGA
GCGGGCTGAGATCTGACGACACGGCCGTGTTTATTACTGTGCGAGAGACT
ATCGGTGGCTGGAACGCTTTGGACGTCTGGGGCCAAGGAACCCTGGTCAC
CGTCTCCTCA V_L chain of #17-190 VL (IGLV1-44*01)(SEQ ID
NO: 43)
CAGCCTGTGCTGACTCAGCCACCCTCAGCGTCTGGGACCCCCGGGCAGAG
GGTCACCATCTCTTGTTCTGGAAGCAGCTCCAACATCGGAATTAATACTG
TAAACTGGTACCAGCAGCTCCCAAGAACGCCCCCCAAACTCCTCATCTAT
ACTAATAATCAGCGGCCCTCAGGGGTCCCTGACCGATTCTCTGGCTCCAA
GTCTGACACCTCAGCCTCCCTGGCCATCAGTGGCCTCCAGTCTGAGGATG
AGGCTGATTATTACTGTGCAGCTTGGGATGACACCCTGAATGGTCCACTA
TTCGGCGGAGGGACCAAGGTGACCGTCCTAGGT Table 11B. #17-190 Variable Region amino acid
sequences V_H chain of #17-190 VH (IGHV1-2*02)(SEQ ID NO: 42)
EVQLVESGAEVKKPGASVKVSCKTSGYTFTDHYTHWVRQAPGQGLEWMGW
INPSSGGTEYAQKFQGRVTMTRDTPISTAYMDLSGLRSDDTAVYYCARET
IGGWNALDVWGQGTLVTVSS V_L chain of #17-190 VL (IGLV1-44*01)(SEQ ID
NO: 44)
QPVLTQPPSASGTPGQRVTISCSGSSSNIGINTVNWYQQLPRTPPKLLIY
TNNQRPSGVPDRFSGSKSDTSASLAISGLQSEDEADYYCAAWDDTLNGPL
FGGGTKVTVLG The huGITR antibodies described herein bind to GITR. In one aspect, the huGITR antibodies have high affinity and high specificity for GITR. In another aspect, the huGITR antibodies can bind the GITR receptor and prevent, inhibit, or block the ligand GITR-L from binding its receptor GITR.

TABLE 12

Amino Acid Sequences of Heavy and Light Chains.

| Antibody | Variable region | CDR1 | CDR2 | CDR3 |
|---|---|---|---|---|
| #1-81 | VH | GYTFTDHY (SEQ ID NO: 45) | INPSSGGT (SEQ ID NO: 46) | ARETIGGWNALDV (SEQ ID NO: 47) |
| #1-81 | VL | SSNIGINT (SEQ ID NO: 48) | TNN (SEQ ID NO: 49) | AAWDDTLNGPL (SEQ ID NO: 50) |
| #3-167 | VH | GYTFTGYY (SEQ ID NO: 51) | INPNSGGT (SEQ ID NO: 52) | AREGVHSDAFDV (SEQ ID NO: 53) |
| #3-167 | VL | QSVYTN (SEQ ID NO: 54) | GAS (SEQ ID NO: 55) | QQYGSSHFT (SEQ ID NO: 56) |

TABLE 12-continued

Amino Acid Sequences of Heavy and Light Chains.

| Antibody | Variable region | CDR1 | CDR2 | CDR3 |
|---|---|---|---|---|
| #5-139 | VH | GYTFTDHY (SEQ ID NO: 57) | INPSSGGT (SEQ ID NO: 58) | ARETIGGWNALDV (SEQ ID NO: 59) |
| #5-139 | VL | SSTIGRHS (SEQ ID NO: 60) | ANN (SEQ ID NO: 61) | AAWDDSLSGVL (SEQ ID NO: 62) |
| #7-192 | VH | GYTFTDHY (SEQ ID NO: 63) | INPSSGG (SEQ ID NO: 64) | ARETIGGWNALDV (SEQ ID NO: 65) |
| #7-192 | VL | KIGTKS (SEQ ID NO: 66) | DDR (SEQ ID NO: 67) | QVWDSNSDHVV (SEQ ID NO: 68) |
| #10-116 | VH | GYTFTGYY (SEQ ID NO: 69) | INPNSGGT (SEQ ID NO: 70) | VREVKDYYYYMDV (SEQ ID NO: 71) |
| #10-116 | VL | SGSIASNS (SEQ ID NO: 72) | DNK (SEQ ID NO: 73) | QSYDDSEQVV (SEQ ID NO: 74) |
| #11-126 | VH | GYTFTGYY (SEQ ID NO: 75) | VNPHSGGT (SEQ ID NO: 76) | ARETDISANYHFDY (SEQ ID NO: 77) |
| #11-126 | VL | SSDVGSYNA (SEQ ID NO: 78) | EVS (SEQ ID NO: 79) | ATWDDSLKGPV (SEQ ID NO: 80) |
| #12-46 | VH | GYTFTGYY (SEQ ID NO: 81) | INPKTGDT (SEQ ID NO: 82) | AREGLSTSSPLDY (SEQ ID NO: 83) |
| #12-46 | VL | ELATNI (SEQ ID NO: 84) | HDN (SEQ ID NO: 85) | QLWDSASDQVV (SEQ ID NO: 86) |
| #13-169 | VH | GYTFTSHY (SEQ ID NO: 87) | INTGNGDT (SEQ ID NO: 88) | ARESSSSWFVAFDV (SEQ ID NO: 89) |
| #13-169 | VL | NIRSKR (SEQ ID NO: 90) | SDN (SEQ ID NO: 91) | QVWDPITDQVV (SEQ ID NO: 92) |
| #14-182 | VH | GYTFTGYY (SEQ ID NO: 93) | INPHSGGT (SEQ ID NO: 94) | AREIV-VVTAPAAAAMDV (SEQ ID NO: 95) |
| #14-182 | VL | SSDVAIYDR (SEQ ID NO: 96) | DVH (SEQ ID NO: 97) | SSYTTSGTFV (SEQ ID NO: 98) |
| #15-68 | VH | GYTFTGYY (SEQ ID NO: 99) | INPNSGGT (SEQ ID NO: 100) | AREGSGDLDSLYMDV (SEQ ID NO: 101) |
| #15-68 | VL | NIGSKS (SEQ ID NO: 102) | DDS (SEQ ID NO: 103) | QLWDGGSDVV (SEQ ID NO: 104) |
| #17-190 | VH | GYTFTDHY (SEQ ID NO: 105) | INPSSGGT (SEQ ID NO: 106) | ARETIGGWNALDV (SEQ ID NO: 107) |
| #17-190 | VL | SSNIGINT (SEQ ID NO: 108) | TNN (SEQ ID NO: 109) | AAWDDTLNGPL (SEQ ID NO: 110) |

The present invention also features antibodies that have a specified percentage identity or similarity to the amino acid or nucleotide sequences of the huGITR antibodies described herein. For example, the antibodies may have 60%, 70%, 75%, 80%, 85%, 90%, 91%, 92%, 93%, 94%, 95%, 96%, 97%, 98%, 99%, or higher identity when compared a specified region or the full length of any one of the huGITR antibodies described herein. Sequence identity or similarity to the nucleic acids and proteins of the present invention can be determined by sequence comparison and/or alignment by methods known in the art. For example, sequence comparison algorithms (i.e. BLAST or BLAST 2.0), manual alignment or visual inspection can be utilized to determine percent sequence identity or similarity for the nucleic acids and proteins of the present invention.

As to amino acid sequences, one of skill in the art will readily recognize that individual substitutions, deletions or additions to a nucleic acid, peptide, polypeptide, or protein sequence which alters, adds, deletes, or substitutes a single amino acid or a small percentage of amino acids in the encoded sequence is collectively referred to herein as a "conservatively modified variant". In some embodiments the alteration results in the substitution of an amino acid with a chemically similar amino acid. Conservative substitution tables providing functionally similar amino acids are well known in the art. Such conservatively modified variants of the huGITR antibody disclosed herein may exhibit increased cross-reactivity to GITR in comparison to an unmodified GITR antibody.

Antibodies

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically binds" or "immunoreacts with" is meant that the antibody reacts with one or more antigenic determinants of the desired antigen and does not react with other polypeptides. Antibodies include, but are not limited to, polyclonal, monoclonal, chimeric, dAb (domain antibody), single chain, $F_{ab}$, $F_{ab'}$ and $F_{(ab')2}$ fragments, scFvs, and $F_{ab}$ expression libraries.

A single chain Fv ("scFv") polypeptide molecule is a covalently linked $V_H$:$V_L$ heterodimer, which can be expressed from a gene fusion including $V_H$- and $V_L$-encoding genes linked by a peptide-encoding linker. (See Huston et al. (1988) Proc Nat Acad Sci USA 85(16):5879-5883). A number of methods have been described to discern chemical structures for converting the naturally aggregated, but chemically separated, light and heavy polypeptide chains from an antibody V region into an scFv molecule, which will fold into a three dimensional structure substantially similar to the structure of an antigen-binding site. See, e.g., U.S. Pat. Nos. 5,091,513; 5,132,405; and 4,946,778.

Very large naïve human scFv libraries have been and can be created to offer a large source of rearranged antibody genes against a plethora of target molecules. Smaller libraries can be constructed from individuals with infectious diseases in order to isolate disease-specific antibodies. (See Barbas et al., Proc. Natl. Acad. Sci. USA 89:9339-43 (1992); Zebedee et al., Proc. Natl. Acad. Sci. USA 89:3175-79 (1992)).

In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, $IgG_3$ and $IgG_4$ and others. Furthermore, in humans, the light chain may be a kappa chain or a lambda chain. The term "antigen-binding site," or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." VH and VL regions, which contain the CDRs, of the scFv antibodies are shown in Tables 1A-Table 11B.

As used herein, the term "epitope" includes any protein determinant capable of specific binding to an immunoglobulin, a scFv, or a T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to a GITR epitope when the equilibrium binding constant ($K_d$) is ≤10 µM, preferably ≤10 nM, more preferably ≤10 nM, and most preferably ≤100 pM to about 1 pM, as measured by assays such as radioligand binding assays or similar assays known to those skilled in the art.

An GITR protein of the invention, or a derivative, fragment, analog, homolog or ortholog thereof, may be utilized as an immunogen in the generation of antibodies that immunospecifically bind these protein components. A GITR protein or a derivative, fragment, analog, homolog, or ortholog thereof, coupled to a proteoliposome may be utilized as an immunogen in the generation of antibodies that immunospecifically bind these protein components.

Those skilled in the art will recognize that it is possible to determine, without undue experimentation, if a human monoclonal antibody has the same specificity as a human monoclonal antibody of the invention by ascertaining whether the former prevents the latter from binding to GITR. If the human monoclonal antibody being tested competes with the human monoclonal antibody of the invention, as shown by a decrease in binding by the human monoclonal antibody of the invention, then it is likely that the two monoclonal antibodies bind to the same, or to a closely related, epitope.

Another way to determine whether a human monoclonal antibody has the specificity of a human monoclonal antibody of the invention is to pre-incubate the human monoclonal antibody of the invention with the GITR protein, with which it is normally reactive, and then add the human monoclonal antibody being tested to determine if the human monoclonal antibody being tested is inhibited in its ability to bind GITR. If the human monoclonal antibody being tested is inhibited then, in all likelihood, it has the same, or functionally equivalent, epitopic specificity as the monoclonal antibody of the invention. Screening of human monoclonal antibodies of the invention can be also carried out by utilizing GITR and determining whether the test monoclonal antibody is able to neutralize GITR.

Various procedures known within the art may be used for the production of polyclonal or monoclonal antibodies directed against a protein of the invention, or against derivatives, fragments, analogs homologs or orthologs thereof (See, for example, Antibodies: A Laboratory Manual, Harlow E, and Lane D, 1988, Cold Spring Harbor Laboratory Press, Cold Spring Harbor, N.Y., incorporated herein by reference).

Antibodies can be purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

The term "monoclonal antibody" or "MAb" or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

Monoclonal antibodies can be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103) Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, *Monoclonal Antibodies: Principles and Practice*, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Fully human antibodies are antibody molecules in which the entire sequence of both the light chain and the heavy chain, including the CDRs, arise from human genes. Such antibodies are termed "humanized antibodies", "human antibodies", or "fully human antibodies" herein. Human monoclonal antibodies can be prepared by using trioma technique; the human B-cell hybridoma technique (see Kozbor, et al., 1983 Immunol Today 4: 72); and the EBV hybridoma technique to produce human monoclonal antibodies (see Cole, et al., 1985 In: Monoclonal Antibodies and Cancer Therapy, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: Monoclonal Antibodies and Cancer Therapy, Alan R. Liss, Inc., pp. 77-96).

In addition, human antibodies can also be produced using additional techniques, including phage display libraries. (See Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al., Bio/Technology 10, 779-783 (1992); Lonberg et al., Nature 368 856-859 (1994); Morrison, Nature 368, 812-13 (1994); Fishwild et al, Nature Biotechnology 14, 845-51 (1996); Neuberger, Nature Biotechnology 14, 826 (1996); and Lonberg and Huszar, Intern. Rev. Immunol. 13 65-93 (1995).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv (scFv) molecules.

An example of a method of producing a nonhuman host, exemplified as a mouse, lacking expression of an endogenous immunoglobulin heavy chain is disclosed in U.S. Pat. No. 5,939,598. It can be obtained by a method, which includes deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

One method for producing an antibody of interest, such as a human antibody, is disclosed in U.S. Pat. No. 5,916,771. This method includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen and a correlative method for selecting an antibody that binds immunospecifically to the relevant epitope with high affinity, are disclosed in PCT publication WO 99/53049.

The antibody can be expressed by a vector containing a DNA segment encoding the single chain antibody described above.

These can include vectors, liposomes, naked DNA, adjuvant-assisted DNA, gene gun, catheters, etc. Vectors include chemical conjugates such as described in WO 93/64701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci USA 87:1149 (1990), Adenovirus Vectors (see LeGal LaSalle et al., Science, 259:988 (1993); Davidson, et al., Nat. Genet 3:219 (1993); Yang, et al., J. Virol. 69:2004 (1995) and Adeno-associated Virus Vectors (see Kaplitt, M. G. et al., Nat. Genet. 8:148 (1994).

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g. adenovirus, HSV) to a desired location. Additionally, the particles can be delivered by intracerebroventricular (icv) infusion using a minipump infusion system, such as a SynchroMed Infusion System. A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266:292-305 (1994)). Other methods that can be used include catheters, intravenous, parenteral, intraperitoneal and subcutaneous injection, and oral or other known routes of administration.

These vectors can be used to express large quantities of antibodies that can be used in a variety of ways. For example, to detect the presence of GITR in a sample. The antibody can also be used to try to bind to and disrupt a GITR activity.

Techniques can be adapted for the production of single-chain antibodies specific to an antigenic protein of the invention (see e.g., U.S. Pat. No. 4,946,778). In addition, methods can be adapted for the construction of $F_{ab}$ expression libraries (see e.g., Huse, et al., 1989 Science 246: 1275-1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Heteroconjugate antibodies are also within the scope of the present invention. Heteroconjugate antibodies are composed of two covalently joined antibodies. Such antibodies have, for example, been proposed to target immune system cells to unwanted cells (see U.S. Pat. No. 4,676,980), and for treatment of HIV infection (see WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

It can be desirable to modify the antibody of the invention with respect to effector function, so as to enhance, e.g., the effectiveness of the antibody in treating cancer. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)).

In certain embodiments, an antibody of the invention may comprise an Fc variant comprising an amino acid substitution which alters the antigen-independent effector functions of the antibody, in particular the circulating half-life of the antibody. Such antibodies exhibit either increased or decreased binding to FcRn when compared to antibodies lacking these substitutions, therefore, have an increased or decreased half-life in serum, respectively. Fc variants with improved affinity for FcRn are anticipated to have longer serum half-lives, and such molecules have useful applications in methods of treating mammals where long half-life of the administered antibody is desired, e.g., to treat a chronic disease or disorder. In contrast, Fc variants with decreased FcRn binding affinity are expected to have shorter half-lives, and such molecules are also useful, for example, for administration to a mammal where a shortened circulation time may be advantageous, e.g. for in vivo diagnostic imaging or in situations where the starting antibody has toxic side effects when present in the circulation for prolonged periods. Fc variants with decreased FcRn binding affinity are also less likely to cross the placenta and, thus, are also useful in the treatment of diseases or disorders in pregnant women. In addition, other applications in which reduced FcRn binding affinity may be desired include those applications in which localization to the brain, kidney, and/or liver is desired. In one exemplary embodiment, the altered antibodies of the invention exhibit reduced transport across the epithelium of kidney glomeruli from the vasculature. In another embodiment, the altered antibodies of the invention exhibit reduced transport across the blood brain barrier (BBB) from the brain, into the vascular space. In one embodiment, an antibody with altered FcRn binding comprises an Fc domain having one or more amino acid substitutions within the "FcRn binding loop" of an Fc domain. The FcRn binding loop is comprised of amino acid residues 280-299 (according to EU numbering). Exemplary amino acid substitutions which altered FcRn binding activity are disclosed in International PCT Publication No. WO05/047327 which is incorporated by reference herein. In certain exemplary embodiments, the antibodies, or fragments thereof, of the invention comprise an Fc domain having one or more of the following substitutions: V284E, H285E, N286D, K290E and S304D (EU numbering).

In some embodiments, mutations are introduced to the constant regions of the mAb such that the antibody dependent cell-mediated cytotoxicity (ADCC) activity of the mAb is altered. For example, the mutation is an LALA mutation in the CH2 domain. In one aspect, the bsAb contains mutations on one scFv unit of the heterodimeric mAb, which reduces the ADCC activity. In another aspect, the mAb contains mutations on both chains of the heterodimeric mAb, which completely ablates the ADCC activity. For example, the mutations introduced one or both scFv units of the mAb are LALA mutations in the CH2 domain. These mAbs with variable ADCC activity can be optimized such that the mAbs exhibits maximal selective killing towards cells that express one antigen that is recognized by the mAb, however exhibits minimal killing towards the second antigen that is recognized by the mAb.

In other embodiments, antibodies, for the diagnostic and treatment methods described herein have a constant region, e.g., an $IgG_1$ or IgG4 heavy chain constant region, which is altered to reduce or eliminate glycosylation. For example, an antibody of the invention may also comprise an Fc variant comprising an amino acid substitution which alters the glycosylation of the antibody. For example, said Fc variant may have reduced glycosylation (e.g., N- or O-linked glycosylation). In exemplary embodiments, the Fc variant comprises reduced glycosylation of the N-linked glycan normally found at amino acid position 297 (EU numbering). In another embodiment, the antibody has an amino acid substitution near or within a glycosylation motif, for example, an N-linked glycosylation motif that contains the amino acid sequence NXT or NXS. In a particular embodiment, the antibody comprises an Fc variant with an amino acid substitution at amino acid position 228 or 299 (EU numbering). In more particular embodiments, the antibody comprises an IgG1 or IgG4 constant region comprising an S228P and a T299A mutation (EU numbering).

Exemplary amino acid substitutions which confer reduced or altered glycosylation are disclosed in International PCT Publication No. WO05/018572, which is incorporated by reference herein. In preferred embodiments, the antibodies, or fragments thereof, of the invention are modified to eliminate glycosylation. Such antibodies, or fragments thereof, may be referred to as "agly" antibodies, or fragments thereof, (e.g. "agly" antibodies). While not being bound by theory, it is believed that "agly" antibodies, or fragments thereof, may have an improved safety and stability profile in vivo. Exemplary agly antibodies, or fragments thereof, comprise an aglycosylated Fc region of an IgG4 antibody which is devoid of Fc-effector function thereby eliminating the potential for Fc mediated toxicity to the normal vital organs that express GITR. In yet other embodiments, antibodies, or fragments thereof, of the invention comprise an altered glycan. For example, the antibody may have a reduced number of fucose residues on an N-glycan at Asn297 of the Fc region, i.e., is afucosylated. In another embodiment, the antibody may have an altered number of sialic acid residues on the N-glycan at Asn297 of the Fc region. iii) Covalent Attachment The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies or to other molecules of the invention. (See, for example, "Conjugate Vaccines", Contributions to Microbiology and Immunology, J. M. Cruse and R. E. Lewis, Jr (eds), Carger Press, N.Y., (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun 133:1335-2549 (1984); Jansen et al., Immunological Reviews 62:185-216 (1982); and Vitetta et al., Science 238:1098 (1987)). Preferred linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxy-sulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction.

Use of Antibodies Against GITR

Antibodies specifically binding a GITR protein or a fragment thereof of the invention can be administered for the treatment a GITR associated disease or disorder. A "GITR-associated disease or disorder" includes disease states and/or symptoms associated with a disease state, where increased levels of GITR and/or activation of cellular signaling pathways involving GITR are found. Exemplary GITR-associated disease or disorder include, but are not limited to, cancer and inflammatory diseases.

Many cancers overexpress GITR and the upregulation of GITR is associated with high risk prognostic factors. Overexpression of GITR or its ligand, GITR-L, in tumor cells can also indicate a mechanism by which the tumor cells evade anti-tumor immunity. Such cancers include solid tumor and hematologic tumor. Use of the antibody of the invention suppress or deplete Tregs and stimulate Teffs. In addition, the antibodies of the invention and increase the toxicity of NK cells and increase IFNγ production.

Antibodies of the invention, including bi-specific, polyclonal, monoclonal, humanized and fully human antibodies, may be used as therapeutic agents. Such agents will generally be employed to treat or prevent cancer in a subject, increase vaccine efficiency or augment a natural immune response. An antibody preparation, preferably one having high specificity and high affinity for its target antigen, is administered to the subject and will generally have an effect due to its binding with the target. Administration of the antibody may abrogate or inhibit or interfere with an activity of the GITR protein.

Antibodies specifically binding a GITR protein or fragment thereof of the invention can be administered for the treatment of a cancer in the form of pharmaceutical compositions. Principles and considerations involved in preparing therapeutic compositions comprising the antibody, as well as guidance in the choice of components are provided, for example, in Remington: The Science And Practice Of Pharmacy 19th ed. (Alfonso R. Gennaro, et al., editors) Mack Pub. Co., Easton, Pa., 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

A therapeutically effective amount of an antibody of the invention relates generally to the amount needed to achieve a therapeutic objective. As noted above, this may be a binding interaction between the antibody and its target antigen that, in certain cases, interferes with the functioning of the target. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine (e.g. IL-15), chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods.

An antibody according to the invention can be used as an agent for detecting the presence of GITR (or a protein or a protein fragment thereof) in a sample. Preferably, the antibody contains a detectable label. Antibodies can be polyclonal, or more preferably, monoclonal. An intact antibody, or a fragment thereof (e.g., $F_{ab}$, scFv, or $F_{(ab)2}$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA includes Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Antibodies directed against a GITR protein (or a fragment thereof) may be used in methods known within the art relating to the localization and/or quantitation of a GITR protein (e.g., for use in measuring levels of the GITR protein within appropriate physiological samples, for use in diagnostic methods, for use in imaging the protein, and the like). In a given embodiment, antibodies specific to a GITR protein, or derivative, fragment, analog or homolog thereof, that contain the antibody derived antigen binding domain, are utilized as pharmacologically active compounds (referred to hereinafter as "Therapeutics").

An antibody specific for a GITR protein of the invention can be used to isolate a GITR polypeptide by standard techniques, such as immunoaffinity, chromatography or immunoprecipitation. Antibodies directed against a GITR protein (or a fragment thereof) can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Pharmaceutical Compositions

The antibodies or agents of the invention (also referred to herein as "active compounds"), and derivatives, fragments, analogs and homologs thereof, can be incorporated into pharmaceutical compositions suitable for administration. Such compositions typically comprise the antibody or agent and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Diagnostic Assays

The huGITR antibodies can be used diagnostically to, for example, monitor the development or progression of a immune cell disorder (e.g., CUL) as part of a clinical testing procedure to, e.g., determine the efficacy of a given treatment and/or prevention regimen.

In some aspects, for diagnostic purposes the huGITR antibody of the invention is linked to a detectable moiety, provides a way for detecting T cell exhaustion in a subject suffering from a cancer or a chronic infection.

The detectable moieties can be conjugated directly to the antibodies or fragments, or indirectly by using, for example, a fluorescent secondary antibody. Direct conjugation can be accomplished by standard chemical coupling of, for example, a fluorophore to the antibody or antibody fragment, or through genetic engineering. Chimeras, or fusion proteins can be constructed which contain an antibody or antibody fragment coupled to a fluorescent or bioluminescent protein. For example, Casadei, et al., describe a method of making a vector construct capable of expressing a fusion protein of aequorin and an antibody gene in mammalian cells.

As used herein, the term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject (such as a biopsy), as well as tissues, cells and fluids present within a subject. That is, the detection method of the invention can be used to detect cells that express GITR in a biological sample in vitro as well as in vivo. For example, in vitro techniques for detection of GITR include enzyme linked immunosorbent assays (ELISAs), Western blots, immunoprecipitations, and immunofluorescence. Furthermore, in vivo techniques for detection of GITR include introducing into a subject a labeled anti-GITR antibody. For example, the antibody can be labeled with a radioactive marker whose presence and location in a subject can be detected by standard imaging techniques. IIn the case of "targeted" conjugates, that is, conjugates which contain a targeting moiety—a molecule or feature designed to localize the conjugate within a subject or animal at a particular site or sites, localization refers to a state when an equilibrium between bound, "localized", and unbound, "free" entities within a subject has been essentially achieved. The rate at which such equilibrium is achieved depends upon the route of administration. For example, a conjugate administered by intravenous injection to localize thrombi may achieve localization, or accumulation at the thrombi, within minutes of injection. On the other hand, a conjugate administered orally to localize an infection in the intestine may take hours to achieve localization. Alternatively, localization may simply refer to the location of the entity within the subject or animal at selected time periods after the entity is administered. By way of another example, localization is achieved when an moiety becomes distributed following administration.

In all of the above cases, a reasonable estimate of the time to achieve localization may be made by one skilled in the art. Furthermore, the state of localization as a function of time may be followed by imaging the detectable moiety (e.g., a light-emitting conjugate) according to the methods of the invention, such as with a photodetector device. The "photodetector device" used should have a high enough sensitivity to enable the imaging of faint light from within a mammal in a reasonable amount of time, and to use the signal from such a device to construct an image.

In cases where it is possible to use light-generating moieties which are extremely bright, and/or to detect light-generating fusion proteins localized near the surface of the subject or animal being imaged, a pair of "night-vision" goggles or a standard high-sensitivity video camera, such as a Silicon Intensified Tube (SIT) camera (e.g., from Hammamatsu Photonic Systems, Bridgewater, N.J.), may be used. More typically, however, a more sensitive method of light detection is required.

In extremely low light levels the photon flux per unit area becomes so low that the scene being imaged no longer appears continuous. Instead, it is represented by individual photons which are both temporally and spatially distinct form one another. Viewed on a monitor, such an image appears as scintillating points of light, each representing a single detected photon. By accumulating these detected photons in a digital image processor over time, an image can be acquired and constructed. In contrast to conventional cameras where the signal at each image point is assigned an intensity value, in photon counting imaging the amplitude of the signal carries no significance. The objective is to simply detect the presence of a signal (photon) and to count the occurrence of the signal with respect to its position over time.

At least two types of photodetector devices, described below, can detect individual photons and generate a signal which can be analyzed by an image processor. Reduced-Noise Photodetection devices achieve sensitivity by reducing the background noise in the photon detector, as opposed to amplifying the photon signal. Noise is reduced primarily by cooling the detector array. The devices include charge coupled device (CCD) cameras referred to as "backthinned", cooled CCD cameras. In the more sensitive instruments, the cooling is achieved using, for example, liquid nitrogen, which brings the temperature of the CCD array to approximately −120° C. "Backthinned" refers to an ultra-thin backplate that reduces the path length that a photon follows to be detected, thereby increasing the quantum efficiency. A particularly sensitive backthinned cryogenic CCD camera is the "TECH 512", a series 200 camera available from Photometrics, Ltd. (Tucson, Ariz.).

"Photon amplification devices" amplify photons before they hit the detection screen. This class includes CCD cameras with intensifiers, such as microchannel intensifiers. A microchannel intensifier typically contains a metal array of channels perpendicular to and co-extensive with the detection screen of the camera. The microchannel array is placed between the sample, subject, or animal to be imaged, and the camera. Most of the photons entering the channels of the array contact a side of a channel before exiting. A voltage applied across the array results in the release of many electrons from each photon collision. The electrons from such a collision exit their channel of origin in a "shotgun" pattern, and are detected by the camera.

Even greater sensitivity can be achieved by placing intensifying microchannel arrays in series, so that electrons generated in the first stage in turn result in an amplified signal of electrons at the second stage. Increases in sensitivity, however, are achieved at the expense of spatial resolution, which decreases with each additional stage of amplification. An exemplary microchannel intensifier-based single-photon detection device is the C2400 series, available from Hamamatsu.

Image processors process signals generated by photodetector devices which count photons in order to construct an image which can be, for example, displayed on a monitor or printed on a video printer. Such image processors are typically sold as part of systems which include the sensitive photon-counting cameras described above, and accordingly, are available from the same sources. The image processors are usually connected to a personal computer, such as an IBM-compatible PC or an Apple Macintosh (Apple Computer, Cupertino, Calif.), which may or may not be included as part of a purchased imaging system. Once the images are in the form of digital files, they can be manipulated by a variety of image processing programs (such as "ADOBE PHOTOSHOP", Adobe Systems, Adobe Systems, Mt. View, Calif.) and printed.

In one embodiment, the biological sample contains protein molecules from the test subject. One preferred biological sample is a peripheral blood leukocyte sample isolated by conventional means from a subject.

The invention also encompasses kits for detecting the presence of GITR or a GITR-expressing cell in a biological sample. For example, the kit can comprise: a labeled compound or agent capable of detecting a cancer or tumor cell (e.g., an anti-GITR scFv or monoclonal antibody) in a biological sample; means for determining the amount of GITR in the sample; and means for comparing the amount of GITR in the sample with a standard. The standard is, in some embodiments, a non-cancer cell or cell extract thereof. The compound or agent can be packaged in a suitable container. The kit can further comprise instructions for using the kit to detect cancer in a sample.

Bi-Specific Antibodies

A bi-specific antibody (bsAb) is an antibody comprising two variable domains or scFv units such that the resulting antibody recognizes two different antigens. The present invention provides for bi-specific antibodies that recognize GITR and a second antigen. Exemplary second antigens include tumor associated antigens, cytokines and cell surface receptors. In some embodiments, the second antigen can be CAIX (carbonic anhydrase IX, or G250), IL-10 or CCR4. In some embodiments, the second antigen can be a cell surface receptor, wherein the cell surface receptor is PD-1, PDL1, CCR4, IL21R, BTLA, HVEM or TIM3. A bi-specific antibody of the present invention comprises a heavy chain and a light chain combination or scFv of the huGITR antibodies disclosed herein.

Construction of Bi-Specific Antibodies

Bi-specific antibodies of the present invention can be constructed using methods known art. In some embodiments, the bi-specific antibody is a single polypeptide wherein the two scFv fragments are joined by a long linker polypeptide, of sufficient length to allow intramolecular association between the two scFv units to form an antibody. In other embodiments, the bi-specific antibody is more than one polypeptide linked by covalent or non-covalent bonds.

In another embodiment, the bi-specific antibody is constructed using the "knob into hole" method (Ridgway et al., Protein Eng 7:617-621 (1996)). In this method, the Ig heavy chains of the two different variable domains are reduced to selectively break the heavy chain pairing while retaining the heavy-light chain pairing. The two heavy-light chain heterodimers that recognize two different antigens are mixed to promote heteroligation pairing, which is mediated through the engineered "knob into holes" of the CH3 domains.

In another embodiment, the bi-specific antibody can be constructed through exchange of heavy-light chain dimers from two or more different antibodies to generate a hybrid antibody where the first heavy-light chain dimer recognizes GITR and the second heavy-light chain dimer recognizes a second antigen. The mechanism for heavy-light chain dimer is similar to the formation of human IgG4, which also functions as a bispecific molecule. Dimerization of IgG heavy chains is driven by intramolecular force, such as the pairing the CH3 domain of each heavy chain and disulfide bridges. Presence of a specific amino acid in the CH3 domain (R409) has been shown to promote dimer exchange and construction of the IgG4 molecules. Heavy chain pairing is also stabilized further by interheavy chain disulfide bridges in the hinge region of the antibody. Specifically, in IgG4, the hinge region contains the amino acid sequence Cys-Pro-Ser-Cys (in comparison to the stable IgG1 hinge region which contains the sequence Cys-Pro-Pro-Cys) at amino acids 226-230. This sequence difference of Serine at position 229 has been linked to the tendency of IgG4 to form novel intrachain disulfides in the hinge region (Van der Neut Kolfschoten, M. et al., 2007, *Science* 317:1554-1557 and Labrijn, A. F. et al, 2011, *Journal of immunol* 187:3238-3246).

Therefore, bi-specific antibodies of the present invention can be created through introduction of the R409 residue in the CH3 domain and the Cys-Pro-Ser-Cys sequence in the hinge region of antibodies that recognize GITR or a second antigen, so that the heavy-light chain dimers exchange to produce an antibody molecule with one heavy-light chain dimer recognizing GITR and the second heavy-light chain dimer recognizing a second antigen, wherein the second antigen is any antigen disclosed herein. Known IgG4 molecules may also be altered such that the heavy and light chains recognize GITR or a second antigen, as disclosed herein. Use of this method for constructing the bi-specific antibodies of the present invention may be beneficial due to the intrinsic characteristic of IgG4 molecules wherein the Fc region differs from other IgG subtypes in that it interacts poorly with effector systems of the immune response, such as complement and Fc receptors expressed by certain white blood cells. This specific property makes these IgG4-based bi-specific antibodies attractive for therapeutic applications, in which the antibody is required to bind the target(s) and functionally alter the signaling pathways associated with the target(s), however not trigger effector activities.

In some embodiments, mutations are introduced to the constant regions of the bsAb such that the antibody dependent cell-mediated cytotoxicity (ADCC) activity of the bsAb is altered. For example, the mutation is an LALA mutation in the CH2 domain. In one aspect, the bsAb contains mutations on one scFv unit of the heterodimeric bsAb, which reduces the ADCC activity. In another aspect, the bsAb contains mutations on both chains of the heterodimeric bsAb, which completely ablates the ADCC activity. For example, the mutations introduced one or both scFv units of the bsAb are LALA mutations in the CH2 domain. These bsAbs with variable ADCC activity can be optimized such that the bsAbs exhibits maximal selective killing towards cells that express one antigen that is recognized by the bsAb, however exhibits minimal killing towards the second antigen that is recognized by the bsAb.

The bi-specific antibodies disclosed herein may be useful in treatment of diseases or medical conditions, for example, cancer. The bi-specific antibodies of the present invention may be particularly useful in diseases or medical conditions that are associated with increased Tregs. I Methods of Treatment The invention provides for both prophylactic and therapeutic methods of treating a subject at risk of (or susceptible to) a cancer, or other cell proliferation-related diseases or disorders. Such diseases or disorders include but are not limited to, e.g., those diseases or disorders associated with aberrant expression of GITR. For example, the methods are used to treat, prevent or alleviate a symptom cancer. Alternatively, the methods are used to treat, prevent or alleviate a symptom of a cancer in which GITR plays a negative regulatory role in T cell response. Alternatively, the methods are used to treat, prevent or alleviate a symptom of a solid tumor such as breast cancer, lung cancer, ovarian cancer, prostate cancer, colon cancer, cervical cancer, brain cancer, skin cancer, liver cancer, pancreatic cancer or stomach cancer. Additionally, the methods of the invention are used to treat hematologic cancers such as leukemia and lymphoma. Alternatively, the methods are used to treat, prevent or alleviate a symptom of a cancer that has metastasized.

Accordingly, in one aspect, the invention provides methods for preventing, treating or alleviating a symptom cancer or a cell proliferative disease or disorder in a subject by administering to the subject a monoclonal antibody, scFv antibody of the invention or bi-specific antibody of the invention. For example, a huGITR antibody may be administered in therapeutically effective amounts.

Subjects at risk for cancer or cell proliferation-related diseases or disorders include patients who have a family history of cancer or a subject exposed to a known or suspected cancer-causing agent. Administration of a prophylactic agent can occur prior to the manifestation of cancer such that the disease is prevented or, alternatively, delayed in its progression.

In another aspect, tumor cell growth is inhibited, Treg activity is decreased, Teff activity is increased, or NK-cell cytotoxicity in increased by contacting a cell with a GITR antibody of the invention. The cell is any cell that expresses GITR. For example the cell is T cell or an NK cell.

Also included in the invention are methods of increasing or enhancing an immune response to an antigen. An immune response is increased or enhanced by administering to the subject a monoclonal antibody or scFv antibody of the invention. The immune response is augmented for example by augmenting antigen specific T effector function. The antigen is a viral (e.g. HIV), bacterial, parasitic or tumor antigen. The immune response is a natural immune response. By natural immune response is meant an immune response that is a result of an infection. The infection is a chronic infection. Increasing or enhancing an immune response to an antigen can be measured by a number of methods known in the art. For example, an immune response can be measured by measuring any one of the following: T cell activity, T cell proliferation, T cell activation, production of effector cytokines, and T cell transcriptional profile.

Alternatively, the immune response is a response induced due to a vaccination. Accordingly, in another aspect the invention provides a method of increasing vaccine efficiency by administering to the subject a monoclonal antibody or scFv antibody of the invention and a vaccine. The antibody and the vaccine are administered sequentially or concurrently. The vaccine is a tumor vaccine a bacterial vaccine or a viral vaccine.

Combinatory Methods

The invention provides treating cancer in a patient by administering two antibodies that bind to the same epitope of the GITR protein or, alternatively, two different epitopes of the GITR protein. Alternatively, the cancer is treated by administering a first antibody that binds to GITR and a second antibody that binds to a protein other than GITR. For example, the other protein other than GITR may include, but is not limited to, PD-1, PD-L1, CAIX, CCR4 and IL-10. For example, the other protein other than GITR is a tumor-associated antigen.

In some embodiments, the invention provides administration of a huGITR antibody alone or with an additional antibody that recognizes another protein other than GITR, with cells that are capable of effecting or augmenting an immune response. For example, these cells may be peripheral blood mononuclear cells (PBMC), or any cell type that is found in PBMC, e.g., cytotoxic T cells, macrophages, and natural killer (NK) cells.

Additionally, the invention provides administration of an antibody that binds to the GITR protein and an anti-neoplastic agent, such a small molecule, a growth factor, a cytokine or other therapeutics including biomolecules such as peptides, peptidomimetics, peptoids, polynucleotides, lipid-derived mediators, small biogenic amines, hormones, neuropeptides, and proteases. Small molecules include, but are not limited to, inorganic molecules and small organic molecules. Suitable growth factors or cytokines include an IL-2, GM-CSF, IL-12, and TNF-alpha. Small molecule libraries are known in the art. (See, Lam, Anticancer Drug Des., 12:145, 1997.)

The invention will be further described in the following examples, which do not limit the scope of the invention described in the claims.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated humanized monoclonal antibody or antigen-binding fragment thereof that binds to the human-glucocorticoid-induced tumor necrosis factor receptor (GITR) comprising
a variable heavy chain region comprising the amino acid sequence of SEQ ID NO: 39, and a variable light chain region comprising the amino acid sequence of SEQ ID NO: 40.

2. An isolated humanized monoclonal antibody or antigen-binding fragment thereof wherein the antibody or antigen-binding fragment comprises
a variable heavy chain complementarity determining region 1, 2, or 3 (VH-CDR) comprising the amino acid sequences of SEQ ID NO. 99, 100, or 101, respectively; and, a variable light chain complementarity determining region 1, 2 or 3 (VL-CDR) comprising the amino acid sequences of SEQ ID NO. 102, 103, or 104, respectively, wherein said antibody or antibody binding fragment binds human-glucocorticoid-induced tumor necrosis factor receptor (GITR).

3. The antibody of claim 1, wherein said antibody is monovalent or bivalent.

4. The antibody of claim 1, wherein said antibody is a single chain antibody.

5. The antibody of claim 1, wherein said antibody has a binding affinity within the range of 10-5 M to 10-12 M.

6. The antibody of claim 1, wherein said antibody has a IgG4 heavy chain constant region.

7. The antibody of claim 1, wherein the Fc region contains mutations at amino acid positions 234 and 235.

8. The antibody of claim 7, wherein the mutations are L234A and L235A.

9. The antibody according to claim 1, wherein said antibody is a bi-specific antibody that also binds to a tumor-associated antigen, a cytokine or a cell surface receptor.

10. The antibody according to claim 1, wherein the antibody is linked to a therapeutic agent.

11. The antibody of claim 10, wherein said therapeutic agent is a toxin, a radiolabel, a siRNA, a small molecule, or a cytokine.

12. A polypeptide comprising the amino acid sequence of SEQ ID NO: 39 or 40.

* * * * *